(12) United States Patent
Fan

(10) Patent No.: US 11,071,753 B2
(45) Date of Patent: *Jul. 27, 2021

(54) MICRO-RNA-155 ENHANCES THE EFFICACY OF DENDRITIC CELL VACCINE FOR CANCER

(71) Applicant: University of South Carolina, Columbia, SC (US)

(72) Inventor: Daping Fan, Columbia, SC (US)

(73) Assignee: University of South Carolina, Columbia, SC (US)

(*) Notice: Subject to any disclaimer, the term of this patent is extended or adjusted under 35 U.S.C. 154(b) by 0 days.

This patent is subject to a terminal disclaimer.

(21) Appl. No.: 16/699,944

(22) Filed: Dec. 2, 2019

(65) Prior Publication Data
US 2020/0093904 A1    Mar. 26, 2020

Related U.S. Application Data

(63) Continuation of application No. 15/477,245, filed on Apr. 3, 2017, now Pat. No. 10,537,625.

(60) Provisional application No. 62/317,964, filed on Apr. 4, 2016.

(51) Int. Cl.
*A61K 35/15* (2015.01)
*A61K 39/00* (2006.01)
*A61P 35/00* (2006.01)

(52) U.S. Cl.
CPC .......... *A61K 35/15* (2013.01); *A61K 39/0011* (2013.01); *A61P 35/00* (2018.01); *A61K 2039/5154* (2013.01); *A61K 2039/5156* (2013.01); *A61K 2039/812* (2018.08)

(58) Field of Classification Search
CPC ................ A61K 35/15; A61K 39/0011; A61K 2039/5156; A61K 2039/812; A61K 2039/5154; A61K 48/00; A61P 35/00
See application file for complete search history.

(56) References Cited

U.S. PATENT DOCUMENTS

| | | | |
|---|---|---|---|
| 10,537,625 B2 * | 1/2020 | Fan .......................... | A61P 35/00 |
| 2016/0008397 A1 * | 1/2016 | Krams ................. | C12N 15/113 |
| | | | 424/278.1 |

OTHER PUBLICATIONS

Zhu et al. (International Journ. Mol. Med (2012), vol. 30: 1321-1326). (Year: 2012).*
Cubillos-Ruiz et al. (Cancer Res. (2012) 72:1683-1693). (Year: 2012).*

* cited by examiner

*Primary Examiner* — J. E. Angell
(74) *Attorney, Agent, or Firm* — Burr & Forman LLP; Douglas L. Lineberry

(57) ABSTRACT

Engineered dendritic cell vaccines, and methods of forming and applying same, that may be used as effective immunotherapies for cancers.

10 Claims, 21 Drawing Sheets

Specification includes a Sequence Listing.

Supplementary Table 1. List of antibodies

| Antibody | Clone (Cat. #) | Application and usage (flow: 1 x 10$^6$ cells) | Company |
|---|---|---|---|
| CD19-FITC | 6D5 (115505) | Flow: 1µl | Biolegend |
| F4/80-FITC | BM8 (11-4801-85) | Flow: 1µl | eBioscience |
| CD11c-APC | N418 (117310) | Flow: 1µl | Biolegend |
| CD11c-FITC | N418 (117306) | Flow: 1µl | Biolegend |
| CD3-PE | 145-2C11 (100308) | Flow: 1µl | Biolegend |
| CD4-APC | GK1.5 (100412) | Flow: 1µl | Biolegend |
| CD8α-FITC | 53-6.7 (100706) | Flow: 1µl | Biolegend |
| CD8α-PE | 53-6.7 (100708) | Flow: 1µl | Biolegend |
| CD206-PE | C068C2 (141706) | Flow: 1µl | Biolegend |
| CD11b-FITC | M1/70 (101206) | Flow: 1µl | Biolegend |
| Gr1-PE | RB6-8C5 (12-5931-83) | Flow: 1µl | eBioscience |
| B220-FITC | RA3-6B2 (103205) | Flow: 1µl | Biolegend |
| MHC II-PE | AF6-120.1 (116407) | Flow: 1µl | Biolegend |
| CD40-FITC | 3/23 (124607) | Flow: 2µl | Biolegend |
| CD40-PE | 3/23 (124610) | Flow: 2µl | Biolegend |
| CD80-FITC | 16-10A1 (104706) | Flow: 1µl | Biolegend |
| CD80-PE | 16-10A1 (12-0801-83) | Flow: 1µl | eBioscience |
| CD86-APC | GL1 (105012) | Flow: 1µl | Biolegend |
| CD86-PE | GL1 (12-0862-83) | Flow: 1µl | eBioscience |
| CCR7-PE | 4B12 (120106) | Flow: 2µl | Biolegend |
| CD45-APC | 30-F11 (103112) | Flow: 1µl | Biolegend |
| CD25-FITC | 3C7 (101908) | Flow: 1µl | Biolegend |
| CD69-FITC | H1.2F3 (104506) | Flow: 1µl | Biolegend |
| IFN-γ-PE | XMG1.2 (505808) | Flow: 1µl | Biolegend |
| IL-6 | MP5-20F3 | Neutralization: 5µg/ml | R&D |
| IL-10 | JES052A5 | Neutralization: 1µg/ml | R&D |
| SOCS1 | GTX100657 | WB: 2µg/ml | GeneTex |
| Jarid2 | ab48137 | WB: 4µg/ml | abcam |
| β-actin | A2066 | WB: 0.4 µg/ml | Sigma |
| H3K27me3 | Ab6002 | ChIP: 4µg/IP | abcam |
| Suz12 | Ab12073 | ChIP: 4µg/IP | abcam |
| IgG | PP64 | ChIP: 4µg/IP | Millipore |

FIGURE 2

A
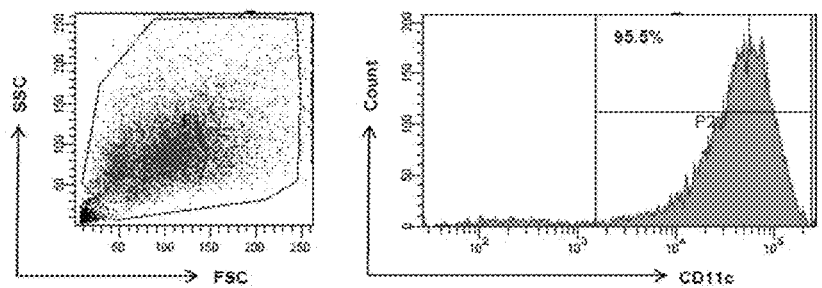
B
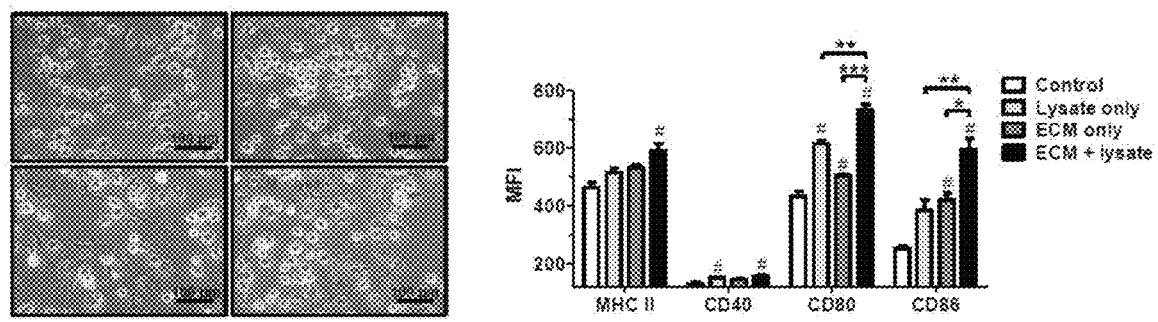
FIGURE 3

Supplementary Table 2. Mouse primers used for Quantitative Real-Time PCR

| Gene Name | Forward (5'----3') | Reverse (5'----3') |
|---|---|---|
| Il-12p35 | GATGACATGGTGAAGACGGC | AGGCACAGGGTCATCATCAA |
| Il-12p40 | GAGAAGGTCACACTGGACCA | TGACCTCCACCTGTGAGTTC |
| Socs1 | TTAACCCGGTACTCCGTGAC | GAGGTCTCCAGCCAGAAGTG |
| c-fos | GGGCTCTCCTGTCAACACAC | CTGGTGGAGATGGCTGTCAC |
| Arg-2 | CTGTGTCACCATGGGAGGAG | GCATGAGCATCAACCCAGAT |
| 18s | CGCGGTTCTATTTTGTTGGT | AGTCGGCATCGTTTATGGTC |
| miR-155 | Cat. #: MS00001701, QIAGEN ||
| U6 | Cat. #: MS00014000, QIAGEN ||
| Ccr7 promoter | TCCCACCCCTCAGAGTCTTC | GGGCTTTCTGAAGGCAAACG |
| Ccr7 intron 1 | TGGTGAGCGGAACTCTAGGA | GCTCCAGACACCCAGTTAC |

FIGURE 4

A
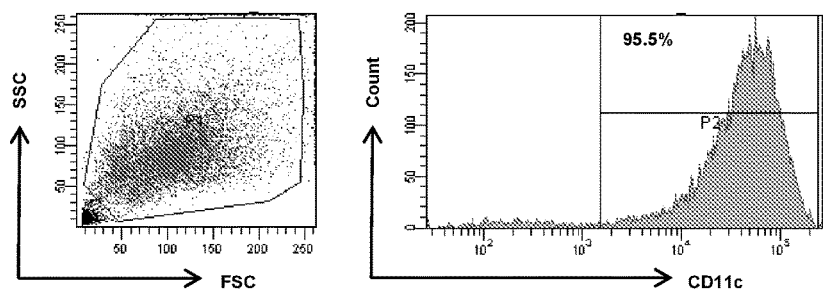
B
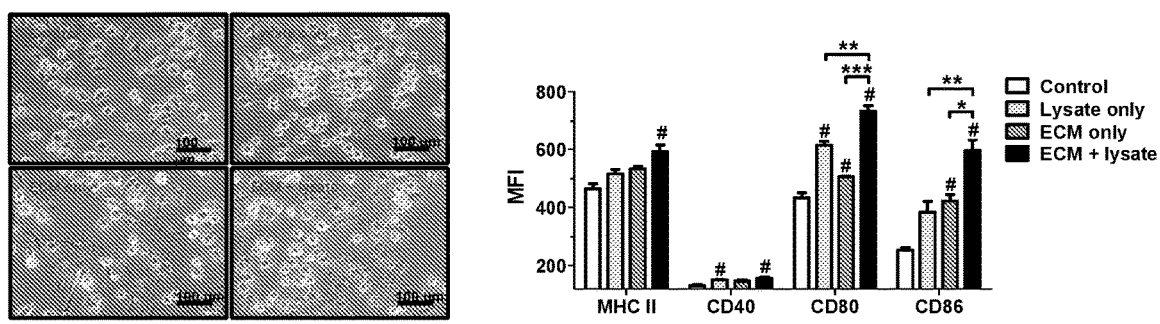
FIGURE 9

MICRO-RNA-155 ENHANCES THE EFFICACY OF DENDRITIC CELL VACCINE FOR CANCER

BACKGROUND OF THE INVENTION

1) Field of the Invention

The present invention relates to engineered dendritic cell vaccines that may be used as effective immunotherapies for cancers.

2) Description of Related Art

Dendritic Cells (DCs) are antigen-presenting cells, also known as accessory cells, of the mammalian immune system. Their main function is to process antigen material and present it on the cell surface to the T cells of the immune system. T cells, or T lymphocytes, are a type of lymphocyte, a subtype of white blood cell, that play a central role in cell-mediated immunity. They can be distinguished from other lymphocytes, such as B cells and natural killer cells, by the presence of a T-cell receptor on the cell surface. They are called T cells because they mature in the thymus from thymocytes, although some also mature in the tonsils. The several subsets of T cells each have a distinct function.

The majority of human T cells rearrange their alpha and beta chains on the cell receptor and are termed alpha beta T cells ($\alpha\beta$ T cells) and are part of the adaptive immune system. Specialized gamma delta T cells, (a small minority of T cells in the human body, more frequent in ruminants), have invariant T cell receptors with limited diversity, that can effectively present antigens to other T cells and are considered to be part of the innate immune system. They act as messengers between the innate and the adaptive immune systems.

Naturally occurring anti-tumor immune responses in cancer patients and in murine tumor models are commonly impaired. Tumor escape as a result of immuno-editing or through local effects of the tumor microenvironment (TME) disables many components of the immune response and ultimately limits the success of immunotherapy. Suppression or modulation of tumor-associated DC function by the TME is thought to play a major role in impairing the development of potent anti-tumor immune responses and promoting tumor progression. Various mechanisms exist by which tumor cells and tumor-associated cells co-opt many endogenous host factors and physiological pathways in order to impair immunogenic DC function.

In anti-tumor immunity, DCs capture, process, and present tumor antigens to T cells, initiating a tumoricidal response to destroy tumor cells. DCs are the most potent professional antigen-presenting cells (APCs), able to activate adaptive immunity through their capacity to sample the environment and capture, process, and present antigens to T cells. Immature DCs in peripheral tissues can capture antigens but due to absence of co-stimulatory molecules, antigen presentation results in induction of tolerance through T-cell deletion, anergy and induction of regulatory, or suppressor T cells. Exposure to pathogens, however, engages the process of maturation which guarantees a well-controlled and targeted immune response.

However, DCs are often dysfunctional due to their exposure to the TME. In early stages of tumor progression, DCs are immunocompetent and able to induce the expansion of specific T-cell responses; however, DCs in advanced tumors become immunosuppressive. The TME is the cellular environment in which the tumor exists, including surrounding blood vessels, immune cells, fibroblasts, bone marrow-derived inflammatory cells, lymphocytes, signaling molecules and the extracellular matrix (ECM). The tumor and the surrounding microenvironment are closely related and interact constantly. Tumors can influence the microenvironment by releasing extracellular signals, promoting tumor angiogenesis and inducing peripheral immune tolerance, while the immune cells in the microenvironment can affect the growth and evolution of cancerous cells, such as in immuno-editing. The TME employs several mechanisms that inhibit DCs to induce efficient anti-tumor responses.

FIG. 1 shows various ways the TME may inhibit DC function. Effector T cells can recognize and kill tumor targets after activation by immunogenic dendritic cells. However, a number of soluble mediators, including TGFβ, IL-10, IL-6, and alarm ins, that are secreted by immunosuppressive cells such as Treg cells, MDSCs, and tumor cells can dysregulate dendritic cells function and limit T-cell effector functions. FIG. 1 path A shows that exposure to pathogens induces the maturation of immunogenic dendritic cells that secrete large amounts of IL-12 upon activation. IL-12 mediates enhancement of the cytotoxic activity of NK cells and $CD8^+$ cytotoxic T lymphocytes, is involved in the differentiation of naive T cells into TH1 cells, and stimulates the production of interferon-gamma (IFN-γ) and tumor necrosis factor-alpha (TNF-α) from T and NK cells. For path B, in the tumor microenvironment, development of detrimental/suboptimal TH2 cells is induced by alarmins such as TSLP, EDN, and MMP-2 through mechanisms depending on inflammatory DCs. In path C, immuno-suppressive cytokines such as IL-10 and TGF-β are responsible for the induction of immature/tolerogenic/immuno-suppressive DCs able to promote the accumulation of regulatory T cells. Tregs play a crucial role in maintaining a suppressive environment and inhibiting anti-tumor responses.

Immunotherapies are becoming a mainstay for several types of cancer. While passive immunotherapies, best represented by T cell immunomodulatory monoclonal antibodies, checkpoint inhibitors, and adoptive T cell transfer, are making their way into clinics, the development of active immunotherapies using tumor antigen-loaded DCs has been relatively stagnant. This is partially due to the lack of understanding of the regulation of DC function in tumors.

About 1 in 8 U.S. women, approximately 12%, will develop invasive breast cancer over the course of her lifetime. DC vaccines are being developed for many cancers, including breast cancer; however, the efficacy of these vaccines is not desirable. Accordingly, it is an object of the present invention to provide engineered DC vaccines that may be used as effective immunotherapies for breast cancer as well as other cancers.

BRIEF DESCRIPTION OF THE DRAWINGS

The construction designed to carry out the invention will hereinafter be described, together with other features thereof. The invention will be more readily understood from a reading of the following specification and by reference to the accompanying drawings forming a part thereof, wherein an example of the invention is shown and wherein:

FIG. 2 shows Supplementary Table 1 which list antibodies used for fluorescein staining.

FIG. 3 shows BMDC identification and maturation.

FIG. 4 displays a table of mouse primers used for Quantitative Real-Time PCR.

FIG. 9 shows BMDC identification and maturation.

Figure 1:
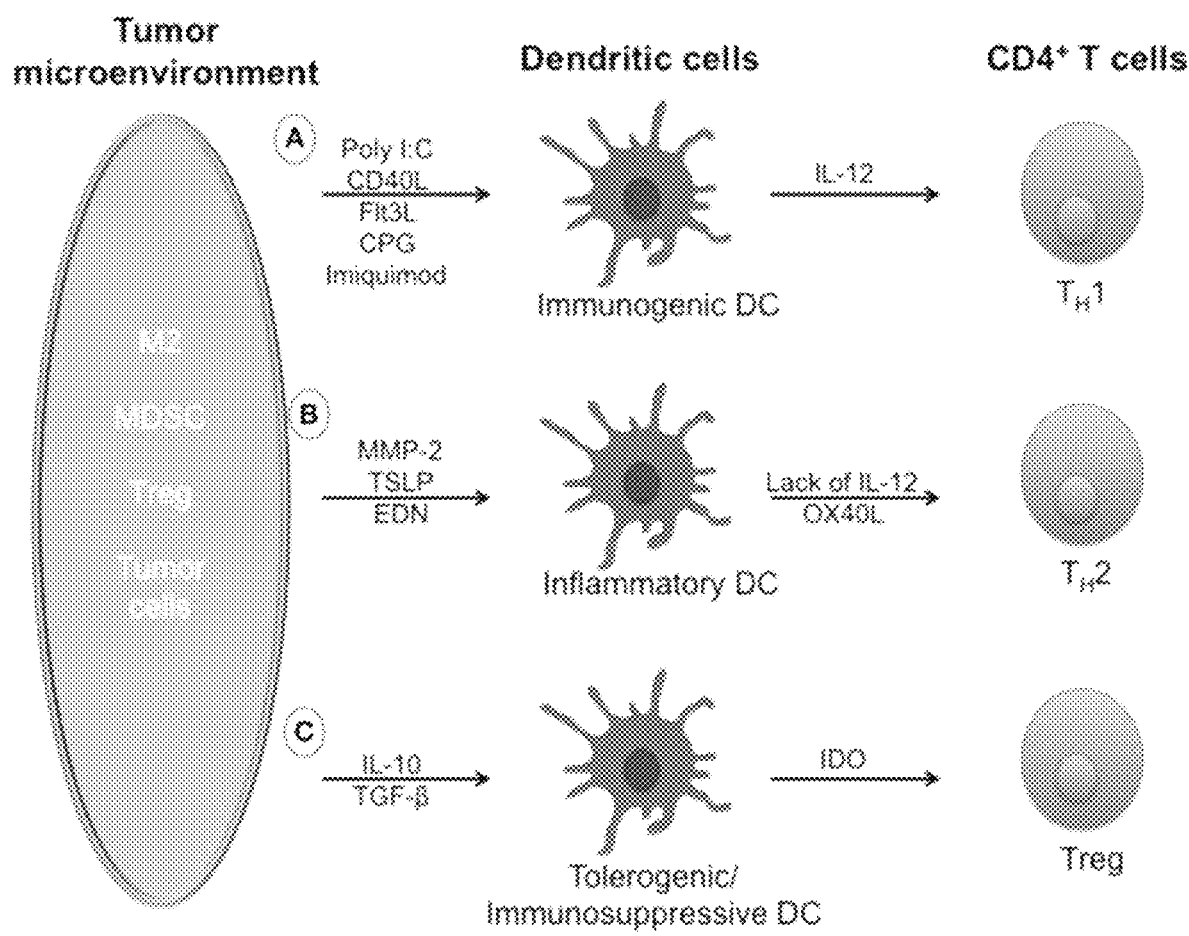
FIG. 1 shows dysregulation of dendritic cell-mediated anti-tumor immune responses by the tumor microenvironment.

It will be understood by those skilled in the art that one or more aspects of this invention can meet certain objectives, while one or more other aspects can meet certain other objectives. Each objective may not apply equally, in all its respects, to every aspect of this invention. As such, the preceding objects can be viewed in the alternative with respect to any one aspect of this invention. These and other objects and features of the invention will become more fully apparent when the following detailed description is read in conjunction with the accompanying figures and examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

SUMMARY OF THE INVENTION

A method for suppressing tumor growth. The method includes amplifying a DNA fragment containing a microRNA segment, sub-cloning the microRNA into a delivery vehicle, delivering the micro-RNA segment to a cell via the delivery vehicle, whereby delivery of the microRNA segment causes the cell to overexpress the micro-RNA segment, followed by injecting the cell into a tumor microenvironment, wherein overexpression of the micro-RNA segment by the cell suppresses tumor growth. Further, the microRNA segment may comprise micro-RNA 155. Still further, the delivery vehicle for the micro-RNA segment may be a viral vector. Even further, the viral vector may comprise a lentivirus or an adenovirus. Further still, the micro-RNA segment is introduced to the cell via electroporation or lipofectamine transfection methods. Furthermore, the delivery vehicle for the micro-RNA segment may be a nanoparticle. The nanoparticle may comprise a liposome or an ionic polymer nanoparticle. Still further, the cell receiving the micro-RNA is a dendritic cell. Even further, the tumor being suppressed may be a breast cancer tumor.

In another embodiment, the current disclosure provides a method for using a lentiviral vector to suppress tumor growth. The method includes amplifying a DNA fragment containing a microRNA stem loop, sub-cloning the DNA fragment containing the microRNA stem loop into a lentiviral vector, delivering the lentiviral vector to a cell, introducing the cell into a tumor microenvironment, whereby delivery of the lentiviral vector containing the micro-RNA causes dendritic cell maturation followed by T-cell activation to suppress tumor growth. Further, the microRNA stem loop may comprise micro-RNA 155. Further yet, the lentiviral vector may comprise PWPI. Still further, the microRNA is introduced to the cell via transfection. Still further, the cell may comprise a dendritic cell. Even further, the tumor being suppressed may be a breast cancer tumor.

DETAILED DESCRIPTION OF A PREFERRED EMBODIMENT

With reference to the drawings, the invention will now be described in more detail. Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are herein described.

Unless specifically stated, terms and phrases used in this document, and variations thereof, unless otherwise expressly stated, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

MicroRNA-155 (miR-155) has been shown to play critical roles in immunity. miR-155 has been identified as an oncogene in several hematological and solid tumors and, thus, miR-155 inhibition has been suggested as an anti-tumor strategy. MicroRNA is a cellular RNA fragment that prevents the production of a particular protein by binding to and destroying the messenger RNA that would have produced the protein. With respect to the current disclosure, the role of miR-155 in DC function was examined in the context of breast cancer and whether manipulation of miR-155 expression in DCs could alter the efficacy of DC-based immunotherapy for breast cancer.

The current disclosure provides that in tumors, the expression of microRNA-155, a small non-coding RNA, is decreased, accompanied by a lost ability in triggering effective anti-tumor immunity. However, when DCs are forced to overexpress microRNA-155, they display significantly enhanced efficacy in suppressing tumor growth and metastasis.

An orthotopic cancer model was employed with an in vitro cell culture system mimicking the TME to examine the effects of miR-155 deficiency on DC function in breast cancer to determine the underlying molecular and epigenetic mechanisms. Antigen-loaded DCs with miR-155 knockout or overexpression were transferred to tumor-bearing mice and therapeutic efficacy was examined.

Host miR-155 deficiency enhanced breast cancer growth in mice, accompanied by compromised DC function. miR-155 expression in DCs correlated with their maturation status, migration ability, cytokine production, and ability to activate T cells. miR-155 regulated DC migration through epigenetic modulation of CCR7 expression. IL-6 and IL-10, two cytokines abundant in the TME, were found to impair DC maturation by suppressing miR-155 expression. Animal studies show that a lack of m iR-155 diminished, while forced expression of miR-155 enhanced, the effectiveness of DC-based immunotherapy for breast cancer. Accordingly, the present disclosure provides that miR-155 is a master regulator of DC function in breast cancer. Boosting the expression of miR-155 may significantly improve the efficacy of DC-based immunotherapies for breast cancer.

In one embodiment of the disclosure, using viral transduction, microRNA transfection, or nanoparticle delivery tools, one can force dendritic cells to overexpress microRNA-155. Lentivirus or adenovirus-associated virus (AAV) based vector harboring microRNA-155 encoding gene can be used to transduce dendritic cells. microRNA-155 mimics can be directly transfected to dendritic cells using electroporation or lipofectamine transfection methods. microRNA-155 mimics can also be incorporated into nanoparticles, such as liposome and cationic polymer nanoparticles, and then delivered to dendritic cells. The vaccine generated using these dendritic cells will display high anti-tumor efficacy. Dendritic vaccines engineered in this manner may be used as effective immunotherapies for breast cancer and other cancers.

Experimental Set-Up: Cell Culture, Tumor Conditioned Medium and Tumor Cell Lysate.

EO771 mouse breast cancer cells, provided by Dr. Jianguo Liu from St. Louis University, were maintained in high-glucose Dulbecco's modified Eagle's medium (DMEM, Invitrogen, Grand Island, N.Y.) supplemented with 10% fetal bovine serum (FBS, Invitrogen) and a combination of penicillin/streptomycin at 37° C. in a humidified 5% $CO_2$ atmosphere.

To obtain tumor conditioned medium, EO771 cells were seeded at $5\times10^6$ cells per 75-$cm^2$ bottle and cultured to 70% confluence. The medium was then replaced with serum-free DMEM. After 48 hours, the culture medium was collected, filtered through 0.45-μm filters, and further concentrated 20-fold using Centrifugal Filters with a 3K molecular weight cut-off (Merck Millipore Ltd.).

For preparation of tumor cell lysate, tumor cells were cultured for 48 h in serum-free DMEM and then disrupted by four freeze-thaw cycles in liquid nitrogen and a 37° C. water bath. The solution was centrifuged at 1,000×g for 10 min to remove insoluble cell fragments, and the supernatant was referred to as cell lysate and used as a source of tumor-associated antigen.

Experimental Set-Up: Orthotopic Breast Cancer Model.

A mouse orthotopic breast cancer model was established. Briefly, $2\times10^5$ EO771 cells in 20 μl of PBS were injected into both sides of the 4th pair of mammary fat pads of WT and miR-155$^{-/-}$ mice. The tumor size was measured using a caliper on indicated days. Tumor volume was determined by the formula: length×width$^2$/2. At the experimental end point, mice were sacrificed; lymph nodes, lungs, tumors, and spleens were removed, weighed, and processed for FACS, immunohistochemistry (IHC) analysis, and other analyses.

Experimental Set-Up: Cell Isolation.

Cells from lymph nodes and spleens were isolated by mechanical disruption. Tumors were weighed, cut into small fragments (<3 mm), and digested in 5 ml of dissociation solution (RPMI 1640 medium supplemented with 10% FBS, Collagenase type 1 (200 U/ml) and DNase 1 (100 μg/ml)) for 1 h at 37° C. Erythrocytes were lysed by red blood cell lysing buffer (Sigma, St. Louis, Mo.). Cell suspensions were passed through 70-μm cell strainers, then washed and resuspended in staining buffer (PBS with 2% FBS).

For DC and T cell purification, $1\times10^8$ cells isolated as described above were sequentially incubated with 20 μl PE-conjugated CD11c or CD3 antibody, 100 μl PE selection cocktail, and 50 μl magnetic nanoparticles (EasySep™ Mouse PE Positive Selection Kit), and then were separated using the magnet according to the manufacturer's instructions. In all samples, a purity of >95% was achieved as determined by flow cytometry.

Experimental Set-Up: Flow Cytometry.

Flow cytometry analysis was performed. Briefly, RBC depleted cells were stained with fluorescein conjugated antibodies, see FIG. 2, Supplementary Table 1, showing the antibodies used for staining, in staining buffer for 30 min on ice, in the dark. Samples were washed twice with staining buffer; cells were acquired using a BD FACS Aria II flow cytometer and data were analyzed by FACSDIVA software. In most cases, 20,000 live events were collected per sample.

Experimental Set-Up: Generation of Bone Marrow-Derived DCs (BMDCs) and Tumor Antigen Pulsing.

Bone marrow cells were flushed from mouse femurs and tibias and erythrocytes were depleted by red blood cell lysing buffer. The resulting cells were cultured at a density of $1\times10^6$ cells/ml in DC medium (RPMI 1640 medium supplemented with 10% FBS and a combination of penicillin/streptomycin, 50 μM β-mercaptoethanol, 10 ng/ml recombinant GM-CSF (rGM-CSF) and 10 ng/ml rIL-4 (BioAbChem Inc. Ladson, S.C.). Fresh medium was added on Day 3. After 7 days of culture, loosely adherent cells were harvested by gentle pipetting (Each preparation was confirmed >90% positive for CD11c (see FIG. 3)) and resuspended in DC medium or treatment medium (DC medium with the addition of 20% (v/v) of concentrated ECM and 100 μg/ml of tumor lysate) to a final density of $0.5\times10^6$ cells/ml and then cultured for 48 h (The combination of tumor lysate and tumor conditioned medium was superior to either lysate or ECM alone in initiating DC maturation (see FIG. 3)).

FIG. 3 shows BMDC identification and maturation. (A) Bone marrow cells were maintained in DC medium for 7 days and its purity was measured by flow cytometry via determining cell surface CD11c expression. (B) Validation of mature BMDC in vitro. WT BMDCs were treated with tumor lysate (100 µg/ml), ECM (20% of 20-fold concentrated EO771 tumor conditioned medium), or both for 48 hours. Cells maintained in DC medium only were used as control. Representative pictures obtained on inverted microscope are shown on the left. Magnification: ×200. Expression of DC maturation markers was determined by flow cytometry. Mean fluorescence intensity (MFI) was quantified, shown on the right. All data are presented as mean±SEM. n=3, $^{\#}$ P<0.05 versus control group; *P<0.05; P<0.005; P<0.005 by one-way ANOVA followed with Tukey multiple comparison test.

BMDCs ($1\times10^5$ cells in 1 ml of DC medium or treatment medium) were placed in 24-well plates for 48 h. Then the supernatant was removed and RPMI 1640 complete medium containing $1\times10^6$ purified CD3$^+$ T cells was added into each well. For T cell activation assays, T cells were harvested after 24 h of co-culture, and cell surface expression of CD25 or CD69 was assessed with flow cytometry. For T cell proliferation assays, cells were co-cultured for 5 days, with 1 µCi [$^3$H] thymidine (Amersham Pharmacia Biotech, Uppsala, Sweden) added to each well during the final 18 h. An equivalent amount of fresh medium was replaced on Day 3. Soluble rIL-2 (20 U/ml, Biolegend) was applied to support the proliferation of purified T cells. Cells were harvested and the incorporated radioactivity was measured in a β-scintillation counter (Microbeta 1450, Wallac, Turku, Finland). Proliferation of T cells or BMDCs alone was examined in parallel as controls.

Experimental Set-Up: Enzyme-Linked Immunosorbent Assay (ELISA).

Cell-free supernatant from BMDC cultures or BMDC/T-cell co-cultures was harvested at the indicated time points. Concentration of IL-12/p70 or IFN-γ was measured. To measure cytokine concentrations in sera, blood samples were collected from WT and miR-155$^{-/-}$ mice bearing breast tumors and allowed to clot for 30 min at room temperature; the samples were then centrifuged at 3,000×g for 10 min; the serum layer was removed and diluted 1:5. Cytokine concentrations were determined by ELISA kits (Biolegend) according to the manufacturer's instructions. All samples were tested in triplicate.

Experimental Set-Up: Quantitative Real-Time PCR (qPCR) for mRNA Expression.

Total RNA was extracted using QIAzol Lysis Reagent (Qiagen, Germantown, Md.). One microgram of RNA from each sample was reverse-transcribed using iScript™ cDNA Synthesis Kits (Bio-Rad Life Science, Hercules, Calif.). qPCR was performed on a Bio-Rad CFX96 system using iQ™ SYBR® Green Supermix (Bio-Rad). All primers used for qPCR analysis were synthesized by Integrated DNA Technologies (Coralville, Iowa). The primer sequences were listed in Supplementary Table 2, see FIG. 4. All assays were performed following the manufacturer's instructions. The relative amount of target mRNA was determined using the comparative threshold (Ct) method by normalizing target mRNA Ct values to those of 18S RNA. PCR thermal cycling conditions were: 3 min at 95° C., 40 cycles of 15 s at 95° C., and 58 s at 60° C. Samples were run in triplicate.

Experimental Set-Up: miR-155 Expression Quantification.

miR-155 expression was measured according to the manufacturer's instructions using the miScript PCR System (QIAGEN, Valencia, Calif.) which is comprised of the miScript Reverse Transcription Kit, miScript SYBR Green PCR Kit, and miScript Primer Assay.

Experimental Set-Up: Western Blot Analysis.

Cells were lysed in RIPA buffer (Pierce, Rockford, Ill.) supplemented with protease inhibitor cocktail and phosphatase inhibitors (Sigma). Total cellular extracts (30 µg) were separated in 4%-20% SDS-PAGE precast gels (Biorad) and transferred onto nitrocellulose membranes (Millipore Corp., Bedford, Mass.). Membranes were first probed with anti-SOCS1 (1:1000, abcam), anti-Jarid2 (1:1000, Genetex) or anti-β-actin (1:1000, Sigma) antibodies, followed by goat anti-rabbit secondary antibody conjugated with HRP (1:5000, Millipore). Protein detection was performed using Pierce ECL Western Blotting Substrate (Pierce).

Experimental Set-Up: In Vivo DC Migration.

Following treatment with tumor lysate and tumor conditioned medium for 48 h, $1\times10^6$ WT or miR-155$^{-/-}$ BMDCs were labeled with CSFE according to the manufacturer's protocol and then injected subcutaneously (s.c.) into the groins of the WT mice implanted with EO771 cells 1 d earlier. Lymph nodes were harvested 48 h after BMDC injection, and CFSE-labeled cells were determined by flow cytometry.

Experimental Set-Up: In Vitro DC Migration.

24-well plates were pre-equilibrated by adding 0.5 ml of serum-free RPMI 1640 medium (SFM) containing 100 ng/ml CCL19 (Sigma, St. Louis, Mo.); then $2\times10^5$ BMDCs in 0.3 ml of RPMI 1640 were seeded into the upper chamber of trans-well inserts with 8 µm pore size (Corning Incorporated Life Sciences, Tewksbury, Mass.) and allowed to migrate for 3 h at 37° C. The upper surfaces of the trans-well inserts were swabbed using cotton buds. Cells that migrated to the lower surfaces were fixed with 4% formaldehyde and stained with DAPI (1 µg/ml) for 1 min. The inserts were then cut out, mounted onto slides and imaged under a Nikon ECLIPSE E600 fluorescence microscope (Nikon Inc. Melville, N.Y.) at 200× magnification (10 fields per membrane, triplicate for each experimental group). DAPI stained cells were quantified using Image-Pro Plus analysis software (Media Cybernetics, Rockville, Md.).

Experimental Set-Up: Chromatin Immunoprecipitation (ChIP) Assay.

BMDCs ($6\times10^6$) seeded in 100-mm dishes were treated with tumor lysate and tumor conditioned medium for 48 h. ChIP assay was performed following standard protocol. In brief, cultures were cross-linked with 1% paraformaldehyde and chromatin was sheared to 200 base pairs. Chromatin (20 µg/IP) was immunoprecipitated with antibodies against histone H3K27me3 or SUZ12, or with a negative control IgG. ChIP-derived DNA was recovered and quantified by qPCR. Data reflects percent input of each qPCR reaction with the indicated primer mixes. Antibodies and validation primers were listed in Supplementary Tables 1 and 2, see FIGS. 2 and 4.

Experimental Set-Up: Lentiviral Vector Construction and Lentiviral Transduction.

General procedures for lentivirus preparation and transduction. Briefly, to generate a lentiviral vector for mouse miR-155 overexpression, a 419-bp DNA fragment containing mouse pre-miR155 stem-loop was amplified by PCR using cDNA from LPS-stimulated C57BL/6 mouse macrophages as a template and then sub-cloned into the bicistronic lentiviral vector PWPI. The miR-155 overexpression construct was verified by DNA sequencing. For viral production, the mouse miR-155 overexpression plasmid, along with the packaging plasmid pCMVΔR8.91 and envelope plasmid pMD2.G were co-transfected into 293T cells using ProFection® mammalian transfection system (Promega) following the manufacturer's instructions. BMDCs were transduced using the RetroNectin-bound Virus Infection method in which lentiviral solutions (MOI=30) were preloaded onto RetroNectin (60 μg/ml, Takara) coated plates according to the manufacturer's instructions. Cells ($0.5 \times 10^6$ in 1 ml) were seeded into lentivirus pre-coated 24-well plates, centrifuged at 2,000×g for 1 h at 25° C. and then incubated for 72 h at 37° C.

Experimental Set-Up: Immunization.

Twenty-four hours post tumor inoculation in WT mice, $0.5 \times 10^6$ tumor-associated antigen pulsed BMDCs were injected s.c. into the groins of the mice once, or twice a week for 3 consecutive weeks for the following experiments: mice injected once with the DC vaccine were sacrificed 48 h later for in vivo T cell activation analysis; mice that received repeated DC immunizations were used for monitoring tumor growth and survival rate.

Experimental Set-Up: Statistical Analysis.

All statistical analysis was performed using the GraphPad Prism software 6.0 (GraphPad Software, Inc., San Diego, Calif.). The data were presented as the mean±SEM. When applicable, unpaired student's t-test, one-way or two-way ANOVA followed by Tukey multiple comparison test were used to determine significance. Survival data were analyzed with the Mantel-Cox log-rank test. $P<0.05$ was considered to be statistically significant.

Results: Host miR-155 Deficiency Enhances Breast Cancer Growth and Metastasis.

The current disclosure, to examine if host miR-155 plays a role in breast cancer, used an orthotopic breast cancer mouse model. WT and miR-155$^{-/-}$ mice were inoculated with EO771 cells in the 4th mammary glands, and tumor growth was monitored. The results showed that host miR-155 deficiency drastically enhanced EO771 tumor growth and metastasis, see FIG. 5, graphs A-C, and FIG. 6A, graph A. The effects were much more robust than those previously observed in melanoma and lung cancer models.

Figure 5:
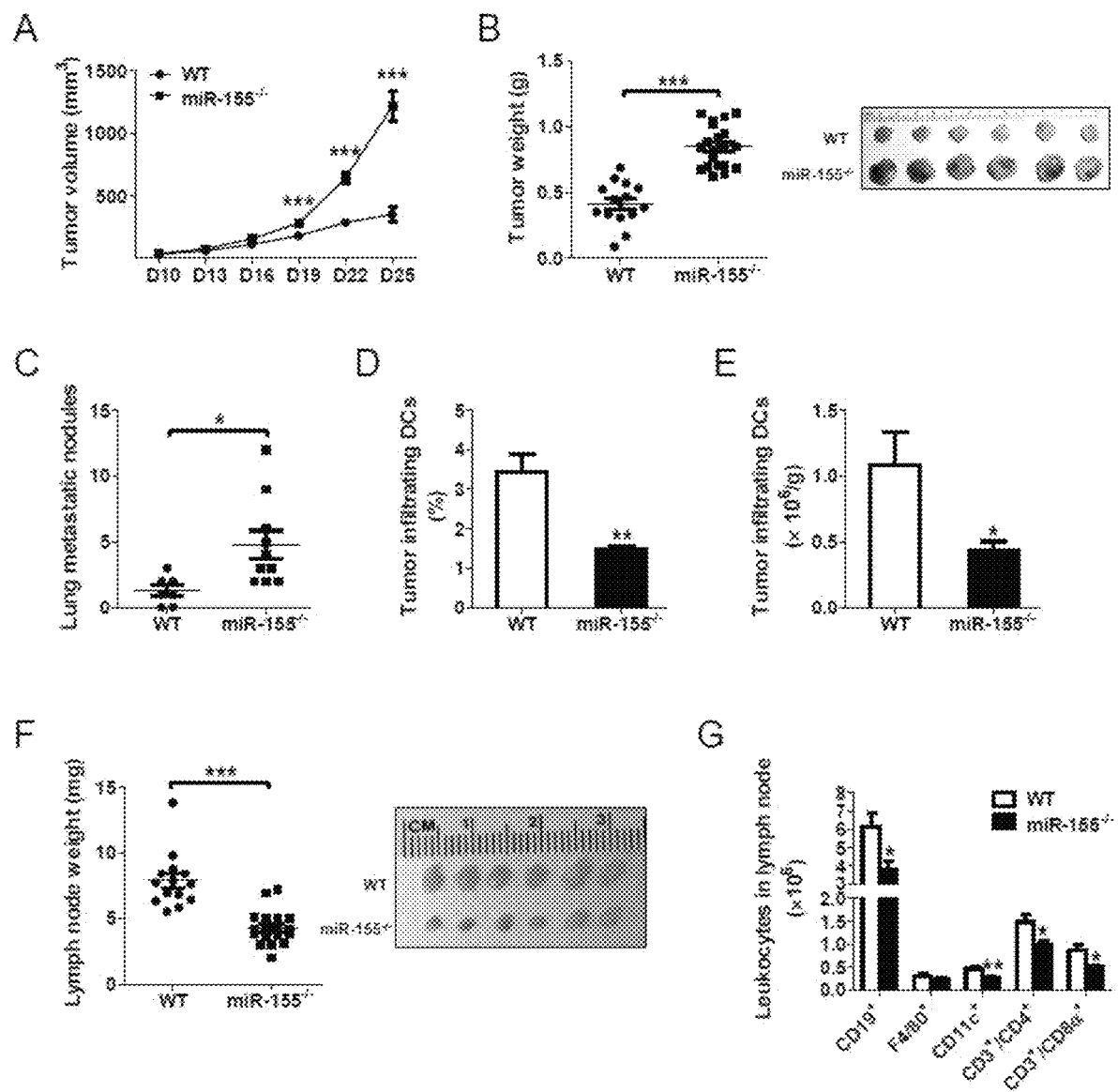
FIG. 5 shows enhanced breast cancer progression and perturbed leukocyte profile in miR-155$^{-/-}$ mice.

FIG. 5 shows enhanced breast cancer progression and perturbed leukocyte profile in miR-155$^{-/-}$ mice. (A) Growth curve of EO771 tumors in WT (n=14) and miR-155$^{-/-}$ mice (n=20). Tumor volume is shown as mm$^3$. Twenty-five days post tumor cell inoculation, tumors and draining lymph nodes were removed and analyzed. (B) Average tumor weight in WT and miR-155$^{-/-}$ mice (left); representative tumors are shown (right). (C) Quantification of tumor nodules per lung in WT (n=7) and miR-155$^{-/-}$ mice (n=10). (D,E) Percentage (D) and absolute cell number (E) of tumor infiltrating DCs per gram tumor tissue of WT and miR-155$^{-/-}$ mice (n=5/group) are shown. (F) Average weight of inguinal lymph nodes (left) and representative tumor draining lymph nodes are shown (right). (G) Absolute cell number of indicated leukocytes within the lymph nodes of WT and miR-155$^{-/-}$ mice (n=5/group). *P<0.05; P<0.01; *P<0.001 by Student's t test.

Figure 6A:
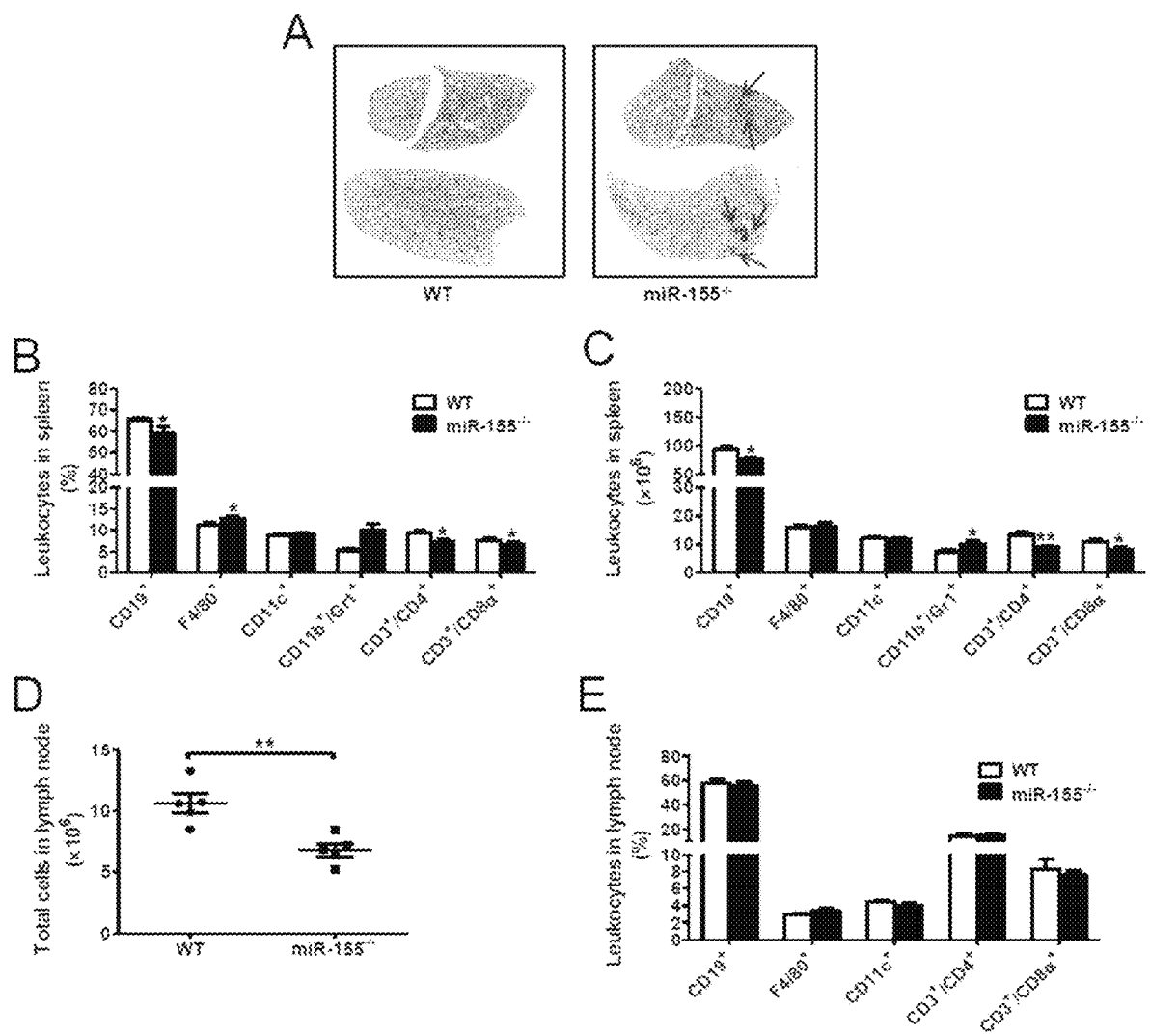
FIGS. 6A and 6B show that miR-155 deficiency promotes breast cancer progression and perturbs leukocyte profile.
Figure 6B:
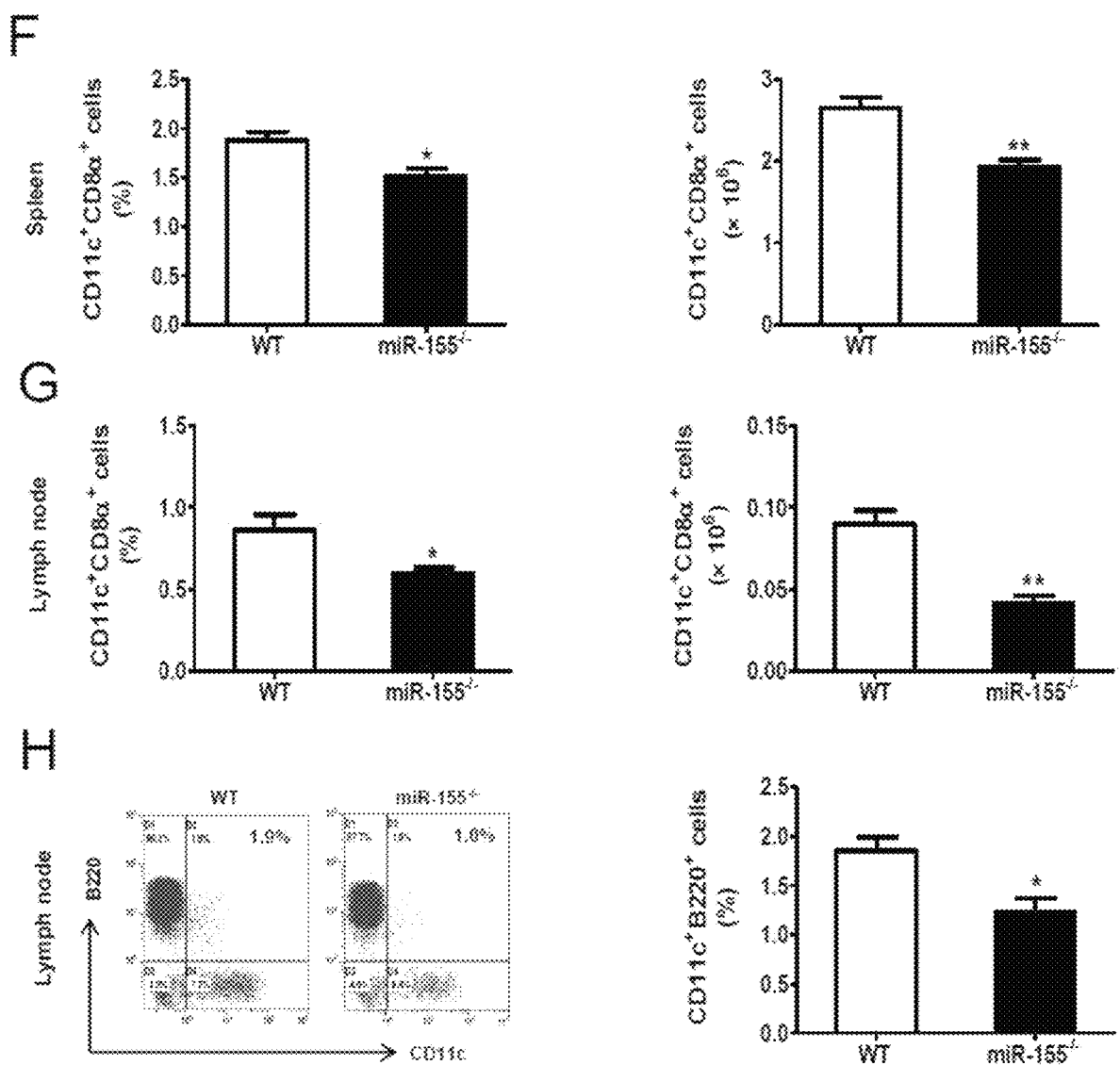

FIGS. 6A and 6B show that miR-155 deficiency promotes breast cancer progression and perturbs leukocyte profile. Twenty-five days post EO771 cell inoculation, lungs, spleens, and tumor draining lymph nodes were removed. (A) Representative H&E staining of lung metastatic nodules are shown. Magnification: ×40. Percentages (B) and absolute cell numbers (C) of indicated leukocytes in spleen. (D) Total cell number in tumor draining lymph nodes. (E) Percentages of indicated leukocytes in tumor draining lymph nodes. (F) Percentage (left) and absolute cell number (right) of CD11c$^+$CD8α$^+$ DCs in spleen. (G) Percentage (left) and absolute cell number (right) of CD11c$^+$CD8α$^+$ DCs in tumor draining lymph nodes. (H) Representative scatter plot (left) and percentage (right) of CD11c$^+$B220$^+$ pDCs in lymph nodes. All data are presented as mean±SEM. n=5, *P<0.05; **P<0.005 by Student's t test.

miR-155 plays pivotal roles in regulating the dynamics and functions of myeloid derived suppressor cells (MDSCs) and tumor associated macrophages (TAMs) in the tumor microenvironment (TME) in melanoma and lung cancer. The current disclosure investigated if host miR-155 deficiency influences immune responses in the breast cancer model. Flow cytometry was performed to determine the leukocyte profile in the spleen, lymph nodes, and tumor tissue. The current disclosure revealed that in the spleens of miR-155$^{-/-}$ breast tumor-bearing mice, there were significantly increased MDSCs and decreased T cells, see FIG. 6A graphs B and C, compared to those in WT mice.

Interestingly, DCs (CD11 c$^+$) were remarkably decreased in the tumor tissue of miR-155$^{-/-}$ mice relative to WT counterparts, see FIG. 6 graphs D and E, while were comparable in spleens, see FIG. 6A graphs B and C. Tumor-bearing miR-155$^{-/-}$ mice had much smaller draining lymph nodes with fewer total cells than WT mice, see FIG. 5 graph F and FIG. 6A, graph D. Flow cytometry analysis showed that lymph nodes of miR-155$^{-/-}$ mice contained much fewer DCs, B cells, and T cells compared to those of WT mice, see FIG. 5, graph G, while the percentages of these cells showed no difference between miR-155$^{-/-}$ and WT mice, see FIG. 6A, graph E.

Furthermore, a remarkable reduction in the classical CD8α+ sub-population of DCs in both the spleen and lymph nodes of tumor-bearing miR-155$^{-/-}$ mice relative to WT mice, see FIG. 6B graphs F and G. These cells are critical to cross-presenting tumor antigens to CD8$^+$ T cells. Meanwhile, another DC sub-population, plasmacytoid DCs (pDC, CD11c$^+$/B220$^+$) were also decreased in the lymph nodes of tumor-bearing miR-155$^{-/-}$ mice, see FIG. 6B, graph H. Taken together, these data suggest that miR-155 deficiency impairs DC maturation and function in breast cancer.

Result: miR-155 is Critical for DC Maturation in Breast Cancer.

In cancer immune surveillance, immature DCs capture tumor antigen and undergo maturation, accompanied by the up-regulation of MHC-II and co-stimulatory molecules as well as the secretion of cytokines. DC maturation is a prerequisite for antigen presentation and T cell activation. miR-155 is required for toll-like receptor ligand-induced DC maturation. The current disclosure, to examine if miR-155 regulates DC maturation in breast cancer, measured MHC-II and costimulatory molecule expression on DCs of multiple organs from WT and miR-155$^{-/-}$ mice carrying EO771 tumors. It was determined that an overall defective pattern of expression of MHC-II and costimulatory markers on splenic DCs, see FIG. 7, graph A and FIG. 8, graph A, tumor infiltrating DCs, see FIG. 7, graph B and FIG. 8, graph B, and lymph node DCs, see FIG. 7, graph C, and FIG. 8, graph C, from miR-155$^{-/-}$ mice compared to WT counterparts. To evaluate the effects of miR-155 deficiency on DC maturation in vitro, bone marrow derived dendritic cells (BMDCs) were generated and pulsed with EO771 cell lysate and EO771 conditioned medium (ECM). The combination of tumor cell lysate and ECM was used because the combination is more effective than either tumor cell lysate or ECM alone in promoting DC maturation, see FIG. 9, insert B. In agreement with the in vivo data, the pulsed miR-155$^{-/-}$ BMDCs exhibited significantly lower expression of maturation markers compared to WT ones, see FIG. 7, graph D; FIG. 8, graph D.

Figure 7:
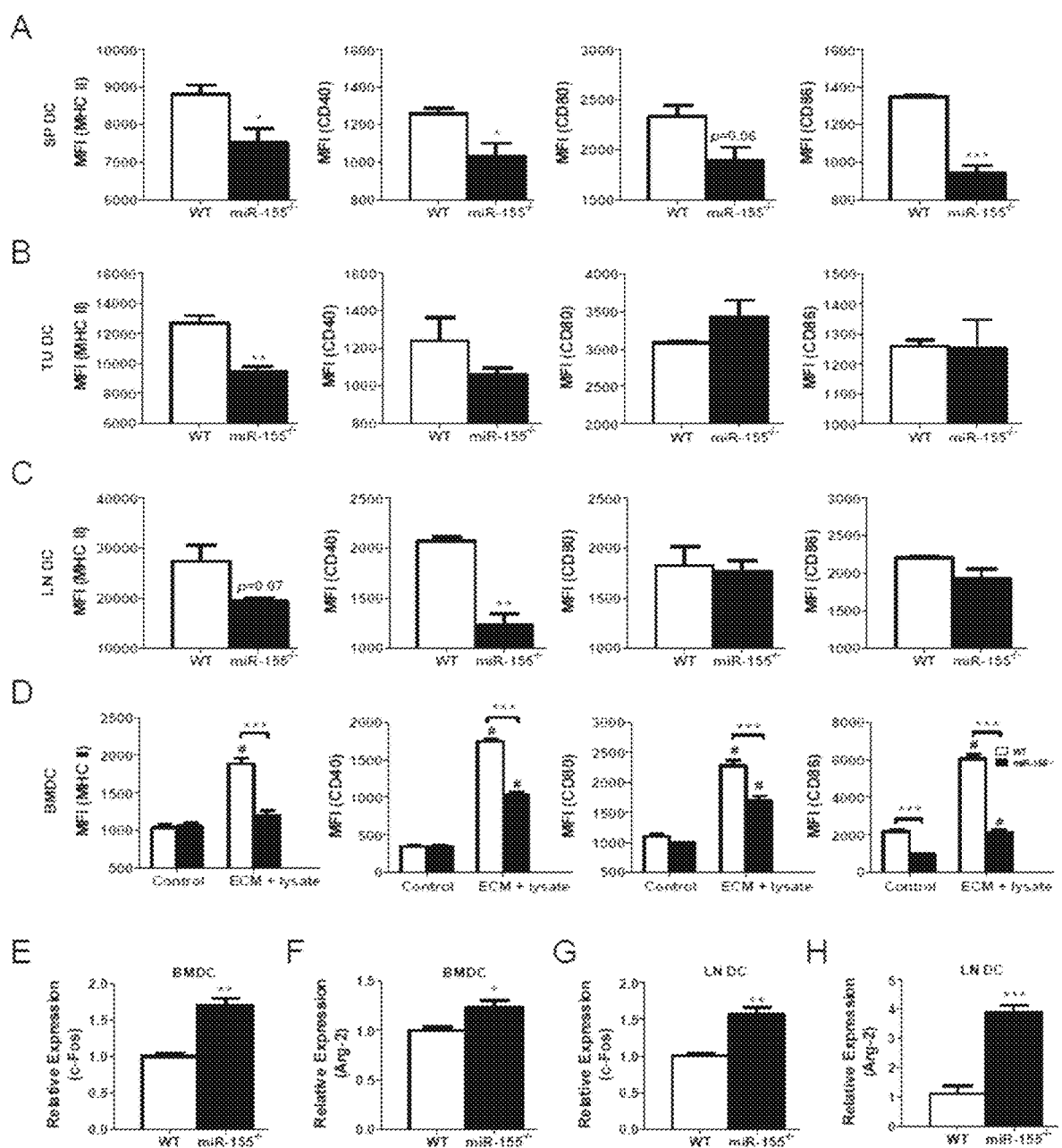
FIG. 7 shows miR-155 deficiency impairs DC maturation.
Figure 8:
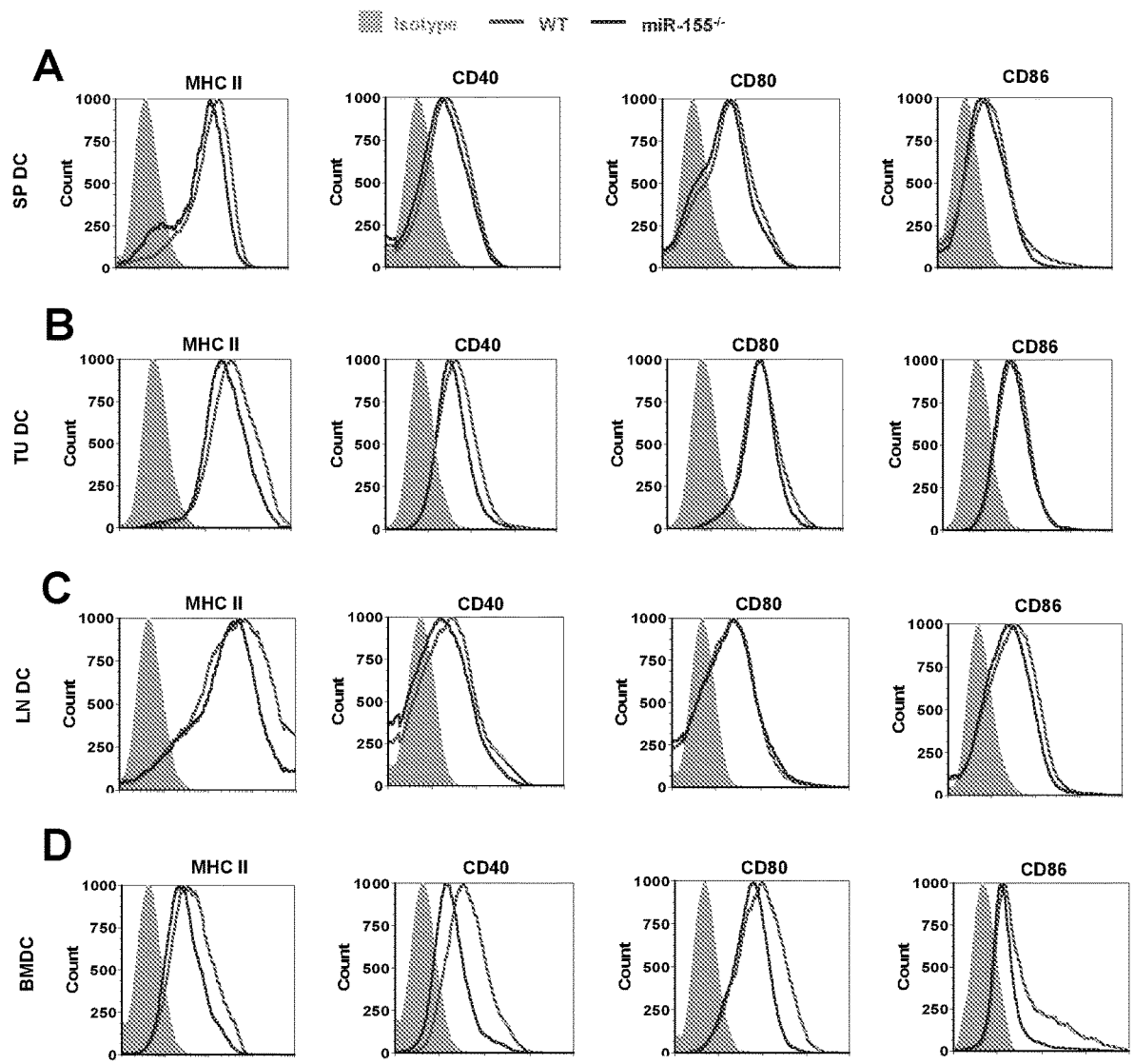
FIG. 8 shows MiR-155 deficiency impairs DC maturation.

FIG. 7 shows miR-155 deficiency impairs DC maturation. Tumor-bearing mice were sacrificed 25 days post inoculation, and single cell suspensions were acquired from spleen, tumor tissue, and lymph nodes. (A-C) Expression of MHC II, CD40, CD80, and CD86 on DCs was analyzed by flow cytometry. Spleen DCs (SP DC) (A) and lymph node DCs (LN DC) (C) were gated from CD11c$^+$ population while tumor infiltrating DCs (TU DC) (B) were gated from CD45$^+$ CD11 c$^+$ population. Mean fluorescence intensity (MFI) of cell markers from 4 experiments were quantified. (D) BMDCs were treated with tumor cell lysate plus ECM in vitro for 48 h and the expression of MHC II, CD40, CD80, and CD86 was determined by flow cytometry (n=3). MFI of cell markers were quantified. (E,F) mRNA levels of c-Fos (E) and Arg-2 (F) in BMDCs treated with tumor cell lysate plus ECM were determined by RT-PCR (n=3). (G,H) mRNA levels of c-Fos (G) and Arg-2 (H) in DCs isolated from tumor draining lymph nodes were determined by RT-PCR (n=3). A-C, E-H, Student's t test; D, two-way ANOVA followed by Tukey multiple comparison test. $^\#$ P<0.05 versus control group; *P<0.05; P<0.01; *P<0.001 versus WT.

FIG. 8 shows MiR-155 deficiency impairs DC maturation. Expression of cell surface MHC II, CD40, CD80, and CD86 in splenic DCs (A), tumor-infiltrating DCs (B), lymph node DCs (C), as well as in vitro tumor-associated antigen matured DCs (D) was analyzed by flow cytometry. Histograms are representative of 3-4 independent experiments.

Repression of c-Fos and Arginase-2, both verified as miR-155 targets, is critical for DC maturation and function in various contexts. To determine if miR-155 affects the expression of these genes in DCs loaded with tumor-associated antigens, BMDCs were treated in vitro with tumor cell lysate and ECM. miR-155$^{-/-}$ BMDCs expressed substantially higher levels of c-Fos and Arg-2 compared to WT ones, see FIG. 7 graphs E and F. Consistent with these findings, both c-Fos and Arg-2 expression levels were significantly enhanced in lymph node DCs of tumor-bearing miR-155$^{-/-}$ mice relative to WT mice, see FIG. 7 graphs G and H. Taken together, these results indicate a requirement of miR-155 expression for efficient maturation of DCs in breast cancer.

Result: miR-155−/− DCs are Defective in Stimulating T Cell Activation and Proliferation.

After maturation, DCs are poised to present antigens to and activate T cells. To examine if miR-155 deficiency in DCs affects their ability to stimulate T cell activation and proliferation, naive splenic T cells were cultured from healthy WT mice with WT or miR-155$^{-/-}$ BMDCs pulsed with tumor cell lysate and ECM. T cell activation induced by pulsed miR-155$^{-/-}$ BMDCs was significantly impaired, characterized by decreased expression of CD25 and CD69, see FIG. 10, graphs A and B. T cell proliferation induced by pulsed miR-155$^{-/-}$ BMDCs was significantly inhibited compared to that induced by WT BMDCs, see FIG. 10, graph C. Furthermore, when co-cultured with miR-155$^{-/-}$ BMDCs pulsed by tumor cell lysate and ECM, T cells displayed a significant decrease in IFN-γ production, see FIG. 10, graph D.

In order for mature DCs to effectively stimulate T cells, not only is antigen-presentation through MHC-antigen complex and co-stimulatory molecules required, but also additional signals such as IL-12 are necessary. IL-12 augments IFN-γ production by CD4$^+$ T cells, NK cells, and CD8$^+$ T cells, and promotes longer conjugation events between CD8$^+$ T cells and DCs. Since miR-155 was reported to regulate IL-12 production by targeting SOCS1 in DCs, the current disclosure determined IL-12 production in DCs in the context of breast cancer. The current disclosure has found that upon tumor cell lysate and ECM treatment, miR-155$^{-/-}$ BMDCs displayed impaired expression of IL-12 mRNAs (both p35 and p40 subunits), see FIG. 10, graphs E and F, and reduced secretion of IL-12p70, see FIG. 10, graph G, compared to WT BMDCs. In agreement with the in vitro data, and found a reduction of both IL-12p70 and IFN-γ concentrations in m mouse sera, see FIG. 10, graphs H and I. As expected, both mRNA and protein levels of SOCS1 were enhanced in miR-155$^{-/-}$ deficient BMDCs treated with tumor cell lysate and ECM, relative to WT BMDCs, see FIG. 10, graphs J and K, suggesting that miR-155 positively regulates IL-12 production in DCs through inhibition of SOCS-1 expression in breast cancer.

Figure 10:
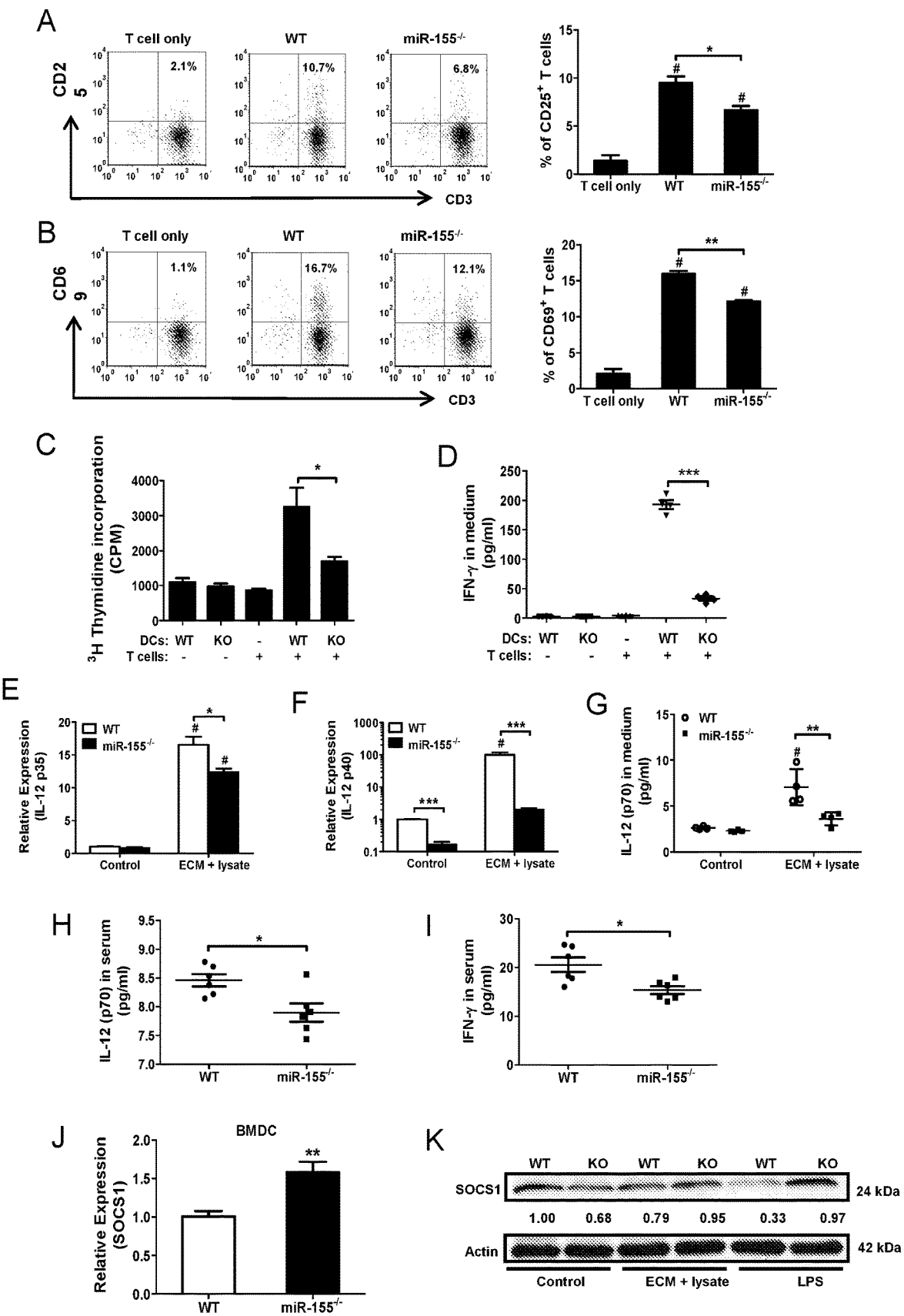
FIG. 10 shows miR-155 is critical for DC-mediated T cell activation.

FIG. 10 shows miR-155 is critical for DC-mediated T cell activation. Naive T cells isolated from spleens of healthy WT mice were co-cultured with tumor cell lysate and ECM pulsed WT or miR-155−/− BMDCs (T cells:DCs=10:1). Twenty-four hours after co-culture, T cell activation was determined by examining CD25 and CD69 expression on CD3$^+$ cells by flow cytometry. T cell only group served as control. (A) Representative scatter plots (left) and percentage of CD3$^+$CD25$^+$ cells (right) are shown (n=3). (B) Representative scatter plots (left) and percentage of CD3$^+$CD69$^+$ cells (right) are shown (n=3). (C) Five days after co-culture, T cell proliferation was measured by [$^3$H] thymidine incorporation assay (n=4). (D) Co-culture media was collected on day 3 and IFN-γ concentrations were measured by ELISA; BMDC and T cell only group were used as controls (n=4). (E,F) mRNA levels of IL-12 p35 (E) and IL-12 p40 (F) were determined by RT-PCR in WT and miR-155$^{-/-}$ BMDCs with or without treatment (n=3). (G) Forty-eight hours post treatment, IL-12 p70 concentrations in BMDC culture media were determined by ELISA; BMDCs without tumor lysate and ECM treatment were used as controls (n=4). (H, I) IL-12 p70 (H) and IFN-γ (I) concentrations in sera of WT and miR-155−/− tumor-bearing mice at the end point (Day 25) were determined by ELISA (n=6). (J,K) mRNA (J) and protein levels (K) of SOCS1 in BMDCs treated with tumor lysate and ECM were determined by RT-PCR and western blot, respectively. LPS stimulated cells were used as positive control. A-D, one-way ANOVA followed by Tukey multiple comparison test. $^\#$ P<0.05 versus T cell only group. E-G, two-way ANOVA following by Tukey multiple comparison test. # P<0.05 versus control group. H-J, Student's t test. *P<0.05; P<0.01; *P<0.001 versus WT group.

Result: miR-155 Deficiency Impairs Dendritic Cell Migration by Suppressing Ccr7 Expression.

To present tumor antigens to and activate T cells, DCs need to migrate to the draining lymph nodes where naïve T cells reside in the deep cortex. To examine if miR-155 deficiency restricts the migratory capacity of DCs to nearby lymph nodes, the current disclosure conducted in vivo DC migration experiments by inoculating CFSE-labeled WT or miR-155$^{-/-}$ DCs pulsed with tumor cell lysate and ECM into the groins of tumor-bearing WT mice. Forty-eight hours later, the percentage of CSFE positive cells in the draining lymph nodes of WT BMDC recipients was 0.32%, while it was only 0.18% in miR-155$^{-/-}$ BMDC recipients, see FIG. 11, graph A. Similarly, in an in vitro migration assay, upon tumor cell lysate and ECM treatment, miR-155$^{-/-}$ BMDCs displayed a defective migratory capacity toward CCL19, see FIG. 11, graph B.

CCR7 is the driving force for DCs to migrate following the CCL19/CCL21 gradient in lymph nodes. The current disclosure measured CCR7 mRNA levels in DCs isolated from tumor-bearing mice, and observed lower CCR7 mRNA expression in spleen, tumor, and lymph node DCs from miR-155$^{-/-}$ mice compared to their WT counterparts, see FIG. 11 graph C. Moreover, miR-155$^{-/-}$ BMDCs, when pulsed with tumor cell lysate and ECM, also exhibited a reduced CCR7 level compared with WT ones, see FIG. 11, graph D. The current disclosure determined cell surface CCR7 expression on DCs by flow cytometry. A significantly lower CCR7 MFI was observed on DCs in the spleen, FIG. 11, graph E, and lymph nodes, FIG. 11, graph F, of tumor-bearing miR-155$^{-/-}$ mice; in vitro matured miR-155$^{-/-}$ BMDCs also exhibited a lower level of CCR7 than WT ones, see FIG. 11, graph G. Taken together, these results indicate that, in breast cancer, reduced CCR7 expression in miR-155$^{-/-}$ DCs may restrain their migration toward lymph nodes.

Figure 11:
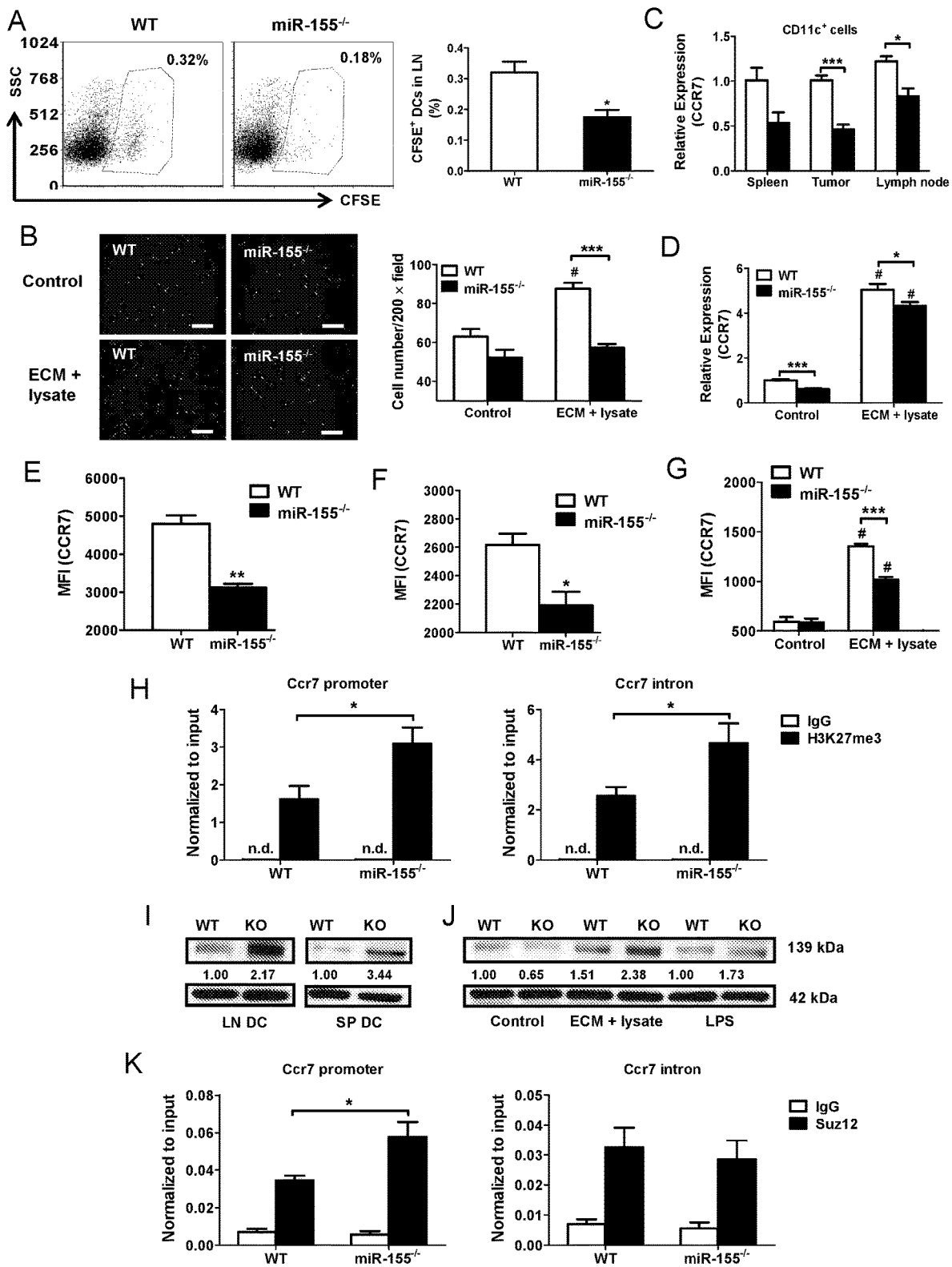
FIG. 11 shows miR-155 affects DC migration by epigenetically regulating CCR7 expression.

FIG. 11 shows miR-155 affects DC migration by epigenetically regulating CCR7 expression. (A) In vivo migration of CFSE-labeled DCs towards draining lymph nodes was measured by flow cytometry. WT or miR-155$^{-/-}$ BMDCs were pulsed with tumor cell lysate and ECM, labeled with CFSE, and implanted into the groins of tumor-bearing WT mice. Typical scatter plots (left) and percentages (right) of CFSE$^+$ population are shown (n=4). (B) In vitro migration of WT or miR-155$^{-/-}$ BMDCs pulsed with tumor cell lysate and ECM was determined by trans-well migration assay. Immature BMDCs maintained in DC medium were used as controls. Representative fluorescence images are shown (left). Cells were counted in 10 random fields per sample at 200× magnification and quantified (right) (n=3). (C) CCR7 mRNA level in DCs isolated from spleen, tumor, and lymph node of WT or miR-155$^{-/-}$ mice carrying EO771 tumors was determined by RT-PCR (n=3). (D) CCR7 mRNA level in BMDCs treated with tumor lysate and ECM in vitro was determined by RT-PCR; immature BMDCs served as controls (n=3). (E,F) Cell surface CCR7 expression on DCs isolated from spleen (E) or lymph node (F) of tumor-bearing WT or miR-155$^{-/-}$ mice was determined by flow cytometry. Representative histograms (upper) and MFI of CCR7 from 3 independent experiments are shown (lower). (G) Representative histogram (upper) and quantified MFI of CCR7 (lower) on BMDCs matured by tumor cell lysate and ECM in vitro are shown. (H) Enrichment of H3K27me3 at Ccr7 promoter (left) and first intron (right) in WT and miR-155$^{-/-}$ BMDCs treated with tumor lysate and ECM was determined by qPCR. Jarid2 protein levels in DCs isolated from lymph nodes and spleens of WT and miR-155$^{-/-}$ tumor-bearing mice (I), and in tumor-associated antigen treated BMDCs (J) were detected by western blot; relative intensities of Jarid2 were labeled under the bands. (K) ChIP-qPCR was performed to detect the recruitment of Suz12 at the Ccr7 promoter (left) and first intron (right) in WT and miR-155$^{-/-}$ BMDCs. A,C,E-F,H,K Student's t test. B,D,G, two-way ANOVA followed by Tukey multiple comparison test. $^{\#}$ P<0.05 versus control group; *P<0.05; P<0.01; *P<0.001 versus WT group.

Result: miR-155 Epigenetically Regulates CCR7 Expression in DCs.

Histone 3 lysine 27 trimethylation (H3K27me3) modulates CCR7 expression in DCs. The current disclosure, in order to investigate if miR-155 regulates CCR7 expression in DCs by affecting H3K27me3, performed a chromatin immunoprecipitation (ChIP) assay. MiR-155$^{-/-}$ BMDCs pulsed with tumor cell lysate and ECM were found to contain significantly more H3K27me3 at the CCR7 promoter and first intron than WT BMDCs, see FIG. 11, graph H. Jumonji, AT Rich Interactive Domain 2 (Jarid2), a direct miR-155 target, recruits Polycomb Repressive Complex 2 (PRC2) to specific sites of the genome and represses target gene expression through H3K27me3. The current disclosure analyzed Jarid2 expression in DCs isolated from spleens and lymph nodes of tumor-bearing mice and observed an increased expression of Jarid2 in miR-155-/- DCs relative to WT ones, see FIG. 11, graph I. A similar result was obtained in miR-155$^{-/-}$ BMDCs when treated with tumor cell lysate and ECM, see FIG. 11, graph J. To determine whether increased Jarid2 in miR-155$^{-/-}$ BMDCs represses CCR7 expression by recruiting PRC2, another ChIP assay was performed to detect a core PRC2 component: Suppressor of Zeste (Suz12); and an increased Suz12 occupancy at the CCR7 promoter was observed in miR-155-/- BMDCs, see FIG. 11, graph K. Taken together, these data suggest that through repressing DNA binding protein Jarid2, miR-155 increases CCR7 expression by diminishing H3K27me3 at the CCR7 locus in DCs.

Result: Tumor Cell-Derived IL-6 and IL-10 Inhibit DC Function Via Repressing miR-155.

As discussed supra, miR-155 is essential for DC maturation and function in the anti-tumor response to breast cancer. The current disclosure proposes that miR-155 up-regulation may be defective in DCs in breast cancer, and thus fewer DCs are sufficiently mature to migrate to lymph nodes and trigger effective anti-tumor immunity, while relatively immature DCs are retained at the tumor site or in circulation. The current disclosure compared miR-155 expression in DCs isolated from lymph nodes, spleen, and tumor tissues of the same tumor-bearing WT mice. The current disclosure observed a significantly lower miR-155 level in splenic and tumor infiltrating DCs compared to that of lymph node DCs, see FIG. 12, graph A. In line with miR-155 expression, the expression of DC maturation markers CD40, CD86, and CCR7 was significantly lower in splenic and tumor infiltrating DCs relative to lymph node DCs, see FIG. 12 graphs B-D and FIG. 13.

Figure 12:
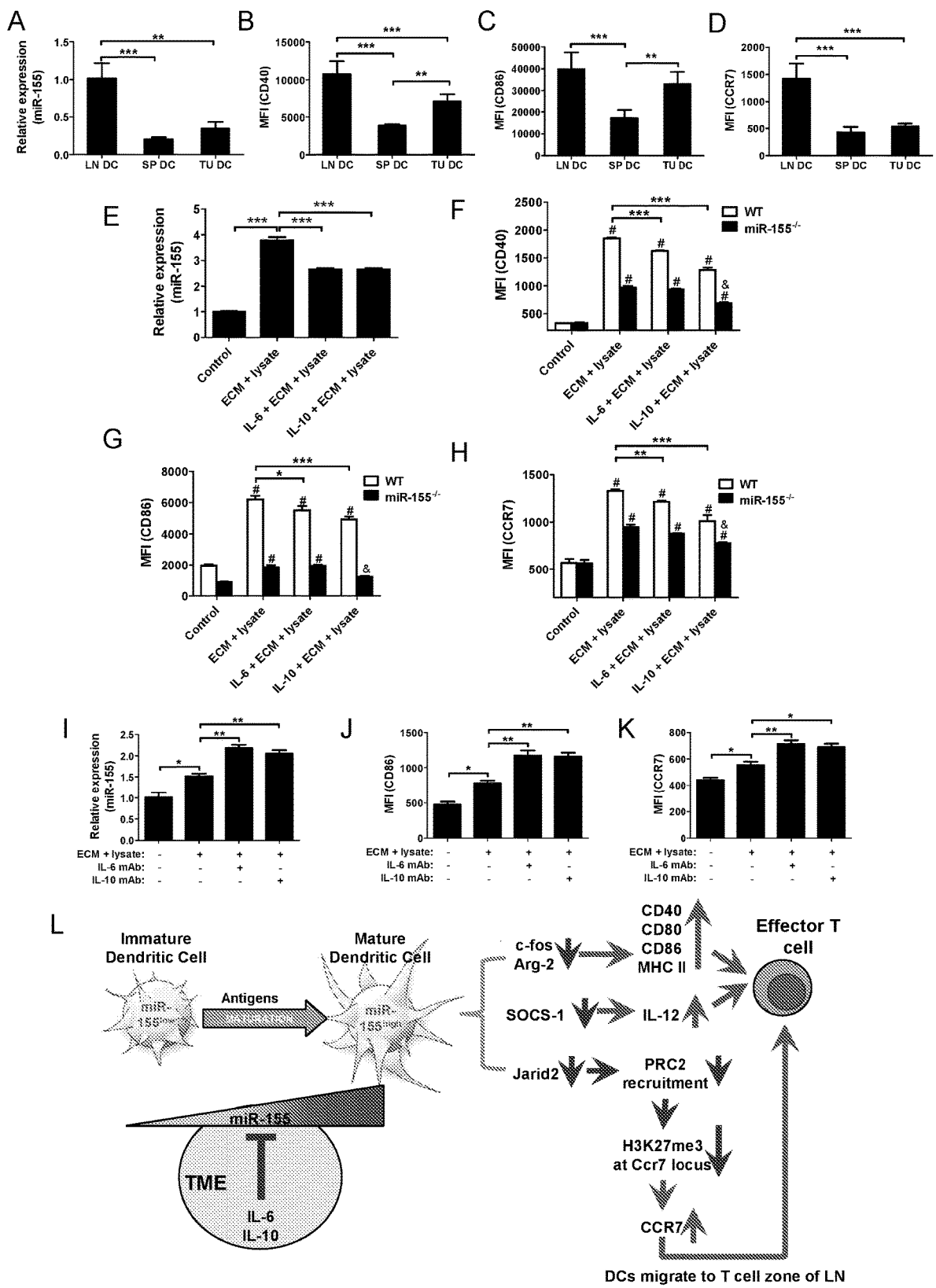
FIG. 12 shows IL-6 and IL-10 inhibit DC maturation through suppressing miR-155.

FIG. 12 shows IL-6 and IL-10 inhibit DC maturation through suppressing miR-155. (A) miR-155 expression in lymph node DCs, splenic DCs, and tumor-infiltrating DCs of tumor-bearing WT mice was detected by RT-PCR (n=3). (B-D) CD40 (B), CD86 (C), and CCR7 (D) expression levels on above DCs were determined by flow cytometry under the same voltage and compensation conditions. (E-H) WT BMDCs were pretreated with IL-6 (100 ng/ml) or IL-10 (50 ng/ml) for 24 h prior to the additional treatment with EO771 tumor cell lysate and ECM; cells without ECM plus cell lysate treatment were used as negative control (n=3). Expression levels of miR-155 (E) and CD40 (F), CD86 (G), and CCR7 (H) were determined by RT-PCR and flow cytometry, respectively. (I-K) To neutralize IL-6 and IL-10 in ECM, IL-6 mAb (5 µg/ml) or IL-10 mAb (1 µg/ml) was added into the treatment medium and incubated for 2 h at 37° C. before BMDC stimulation (n=3). Expression of miR-155 (I), CD86 (J), and CCR7 (K) were determined by RT-PCR and flow cytometry, respectively. A-E, I-K, one-way ANOVA followed by Tukey multiple comparison test; F-H, two-way ANOVA followed by Tukey multiple comparison test. $^{\#}$ P<0.05 versus their respective control group; &P<0.05 relative to positive control; *P<0.05; P<0.01; *P<0.001. (L) Schematic graph depicting the molecular mechanisms underlying miR-155-mediated anti-tumor immune response in DCs. During early tumor development, immature DCs recognize and take up tumor antigens, resulting in elevated miR-155 expression, which affects the following three functions of DCs: (1) DC maturation: Upregulation of MHC II and costimulatory molecules (CD40, CD80 and CD86) by miR-155-mediated suppression of c-Fos and Arg-2 contributes to DCs maturation; (2) T cell activation: Enhanced IL-12 p70 production by miR-155 via inhibiting SOCS1 is essential to elicit T cell activation; and (3) DC migration: miR-155 reduces H3K27me3 enrichment at the Ccr7 locus through repressing Jarid2 expression and PRC2 recruitment. Elevated CCR7 expression drives DCs migration toward the T cell zone of draining lymph nodes, where DCs activate effector T cells and initiate a tumor specific immune response. However, with the development of breast cancer, miR-155 expression is repressed by gradually elevated soluble factors (such as IL-6 and IL-10), mainly secreted by tumor cells and immunosuppressive cells in the TME, leading to DC dysfunction and ultimately tumor escape from immune surveillance.

Figure 13:
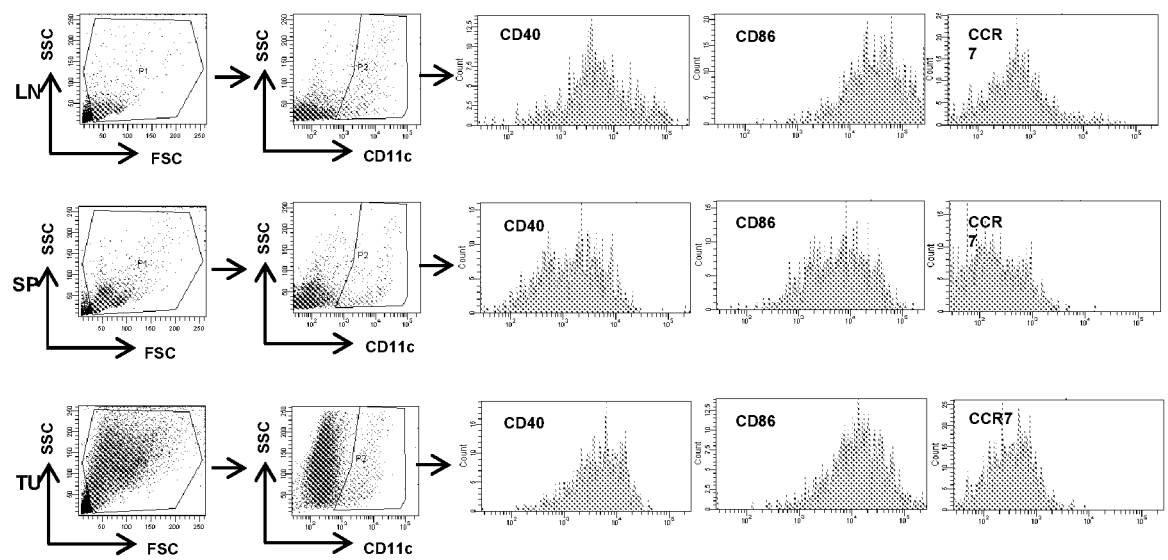
FIG. 13 shows a comparison of DC maturation status among lymph node, spleen, and tumor infiltrating DCs.

FIG. 13 shows a comparison of DC maturation status among lymph node, spleen, and tumor infiltrating DCs. Twenty-five days post EO771 cell inoculation, DC maturation status in lymph node, spleen, and tumor were compared via determining the indicated maturation markers under the same voltage and compensation conditions by flow cytometry. Typical scatter plots and histograms from 3 independent experiments are shown.

DCs in the TME possess a relatively immature phenotype, and the dysfunction of DCs in tumors may be results from their exposure to soluble factors, such as IL-10 and IL-6, in the TME. To elucidate if these soluble factors inhibit DC maturation via suppressing miR-155 expression, the current disclosure conducted in vitro experiments by pretreating WT and miR-155$^{-/-}$ BMDCs with IL-6 or IL-10 before pulsing them with maturation stimuli. The current disclosure found that both IL-6 and IL-10 pretreatment significantly inhibited miR-155 expression, see FIG. 12, graph E, and maturation of WT BMDCs, see FIG. 12, graphs F-H. Conversely, depletion of IL-6 or IL-10 using neutralizing antibodies significantly elevated the expression of miR-155, see FIG. 12, graph I, and DC maturation markers, see FIG. 12, graphs J and K.

Taken together, these results demonstrate that some soluble factors in the TME, such as IL-6 and IL-10, impair DC maturation through diminishing miR-155 up-regulation, see FIG. 12, graph L, although some other soluble factors may enhance DC maturation since tumor cell lysate plus ECM is more effective than tumor cell lysate alone in priming DCs, see FIG. 9, graph B. Therefore, targeted removal of these inhibitory soluble factors or forced miR-155 expression in DCs may unleash the full potential of DCs to trigger anti-tumor immunity in breast cancer.

Result: Impact of miR-155 Expression on the Efficacy of DC-Based Immunotherapy for Breast Cancer.

Per the current disclosure, to confirm the contribution of DC miR-155 to the anti-tumor immune response to breast cancer, mice carrying orthotopic EO771 breast tumors were adoptively transferred with WT or miR-155$^{-/-}$ BMDCs pulsed with tumor cell lysate and ECM. A set of mice were sacrificed 48 h after the first DC vaccine administration, and enlargement of both draining lymph nodes and spleens were observed in WT but not in miR-155$^{-/-}$ BMDC treated mice, see FIG. 14, graphs A and C. Also, an augmentation of activated T cells was only detected in the draining lymph nodes of WT BMDC transferred mice, see FIG. 14, graphs B and D. Although these differences disappeared 5 days post DC transfer, see FIG. 15, significantly smaller tumors were observed in mice that received WT MDSCs but not in those received miR-155$^{-/-}$ ones, see FIG. 14, graph E. To monitor tumor growth and survival rate, additional DC vaccine was injected twice a week for 3 consecutive weeks in another set of mice. Although tumor growth rates in both groups were restricted compared to control mice, miR-155$^{-/-}$ deficient DCs showed less beneficial effects, see FIG. 14, graph F. In addition, WT DC treated mice survived much longer than the miR-155$^{-/-}$ DC group, see FIG. 14, graph G.

Figure 14:
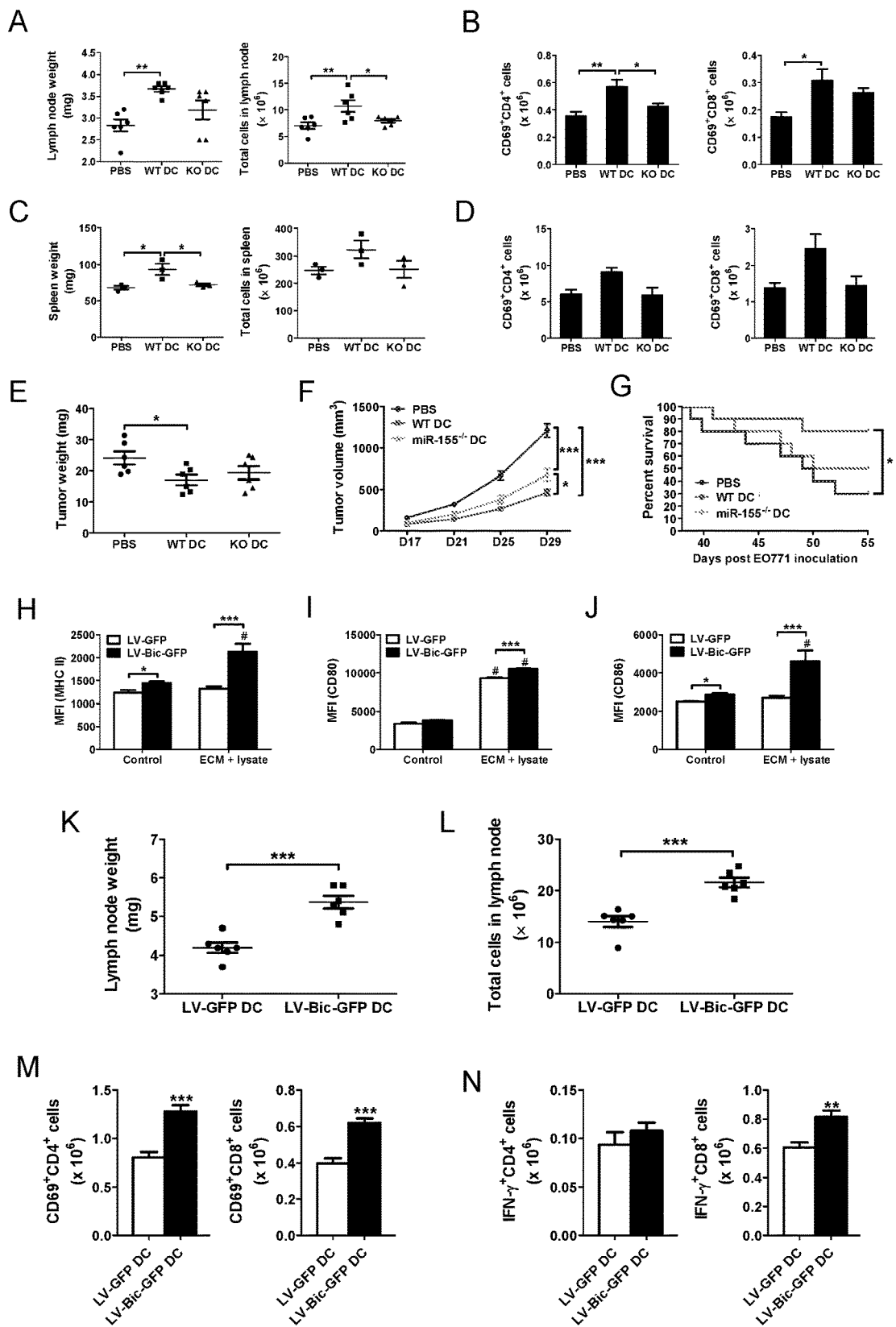
FIG. 14 shows miR-155 expression level determines the efficacy of DC-based immunotherapy for breast cancer.

FIG. 14 shows miR-155 expression level determines the efficacy of DC-based immunotherapy for breast cancer. WT mice were implanted with EO771 tumor cells; 24 h later, WT BMDCs (WT DC) or miR-155$^{-/-}$ BMDCs (KO DC) matured by tumor cell lysate and ECM in vitro were injected s.c. as vaccines. (A-D) Forty-eight hours post DC vaccination, lymph nodes and spleens were removed. Mice injected with PBS served as control. Lymph nodes were weighed (left) and absolute cell numbers in lymph nodes were counted (right) (A). Activated CD4$^+$ T cells (left) and CD8$^+$ T cells (right) in lymph nodes were measured by flow cytometry (B). Spleens were weighed (left) and absolute cell numbers in spleens were counted (right) (C). Activated CD4$^+$ T cells (left) and CD8$^+$ T cells in spleens were measured by flow cytometry (D). (E) Five days post DC vaccination, some mice were sacrificed and tumors were weighed. (F,G) DC vaccine was injected twice a week for consecutive 3 weeks in some mice; growth kinetics of EO771 tumors was followed until Day 29 after tumor inoculation (F), and survival rates of tumor-bearing mice were monitored until Day 55 after tumor inoculation (G). (H-J) WT BMDCs were transduced with miR-155 overexpression (LV-Bic-GFP) or control lentivirus (LV-GFP) and treated with tumor lysate and ECM. 48 h later, CD11c$^+$GFP$^+$ cells were gated and expression of DC maturation markers MHCII (H), CD80 (I) and CD86 (J) were determined by flow cytometry. (K-N) WT mice were injected s.c. with lentivirus-transduced BMDCs once 24 h after EO771 cell inoculation. Forty-eight hours later, mice were sacrificed; draining lymph node weight (K), numbers of total leukocyte per lymph node (L), absolute activated T cells (M), and INF-γ-producing T cells (N) were measured. A-F, one-way ANOVA followed by Tukey multiple comparison test. G, Survival data were analyzed with the Mantel-Cox log-rank test. *P<0.05; P<0.01; *P<0.001. H-J, two-way ANOVA followed by Tukey multiple comparison test; K-N, Student's t test. $^\#$ P<0.05 versus their control counterparts; *P<0.05; P<0.01; *P<0.001 versus LV-GFP DC group.

Figure 15:
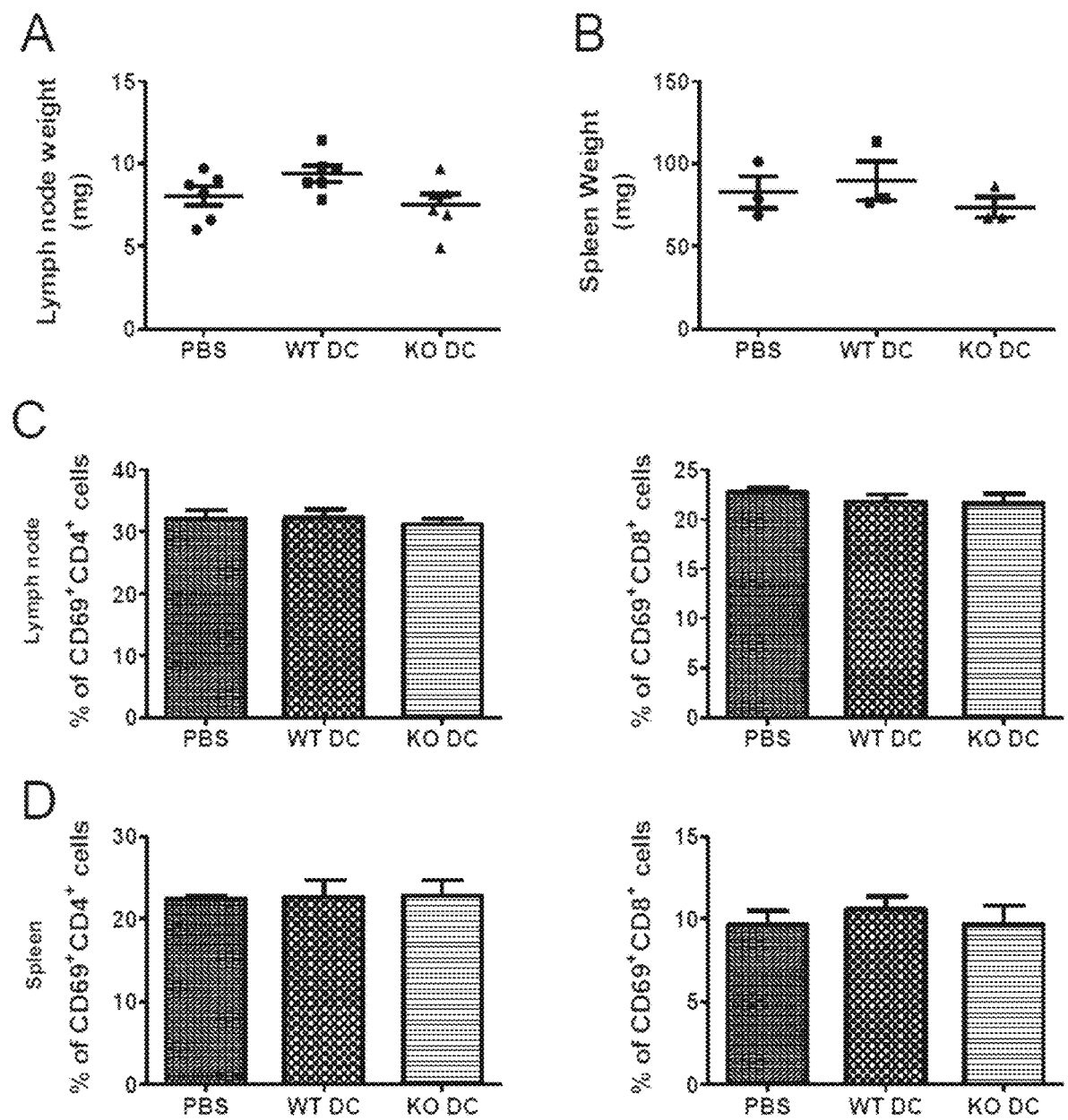
FIG. 15 shows T cell activation post BMDC immunization in vivo. 5 days post DC vaccination, lymph nodes, and spleens were removed, and activated T cell (CD69$^+$) contents were determined by flow cytometry.

FIG. 15 shows T cell activation post BMDC immunization in vivo. 5 days post DC vaccination, lymph nodes, and spleens were removed, and activated T cell (CD69$^+$) contents were determined by flow cytometry. Lymph node weight (A) and spleen weight (B) were shown. (C) Percentage of activated CD4+ T cells (left) and CD8$^+$ T cells (right) in the draining lymph nodes (n=6). (D) Percentage of activated CD4+ T cells (left) and CD8$^+$ T cells (right) in the spleens (n=3). All data were analyzed by one-way ANOVA followed by Tukey multiple comparison test.

To explore the translatability of these findings, miR-155-overexpressing BMDCs were generated by lentiviral transduction using bicistronic lentiviral vectors (34). The transduction efficiency was ~20% and overall miR-155 expression level was increased ~1.7-fold, see FIG. 16. Despite the low positivity, miR-155 lentivirus transduced BMDCs exhibited significantly higher expression of DC maturation markers than control lentivirus transduced cells after pulsation, see FIG. 14, graphs H-J. In miR-155 lentivirus transduced BMDC administered tumor-carrying mice, larger lymph nodes, see FIG. 14, graphs K and L, with larger activated T cell populations, see FIG. 14, graphs M and N) were observed 48 h after DC administration compared to those in control DC injected mice. Spleen sizes and cell numbers, and activated T cell populations showed no significant difference between the two groups, see FIG. 17. These results indicate that a stronger early anti-tumor immune response was elicited by miR-155-overexpressing DCs.

Figure 16:
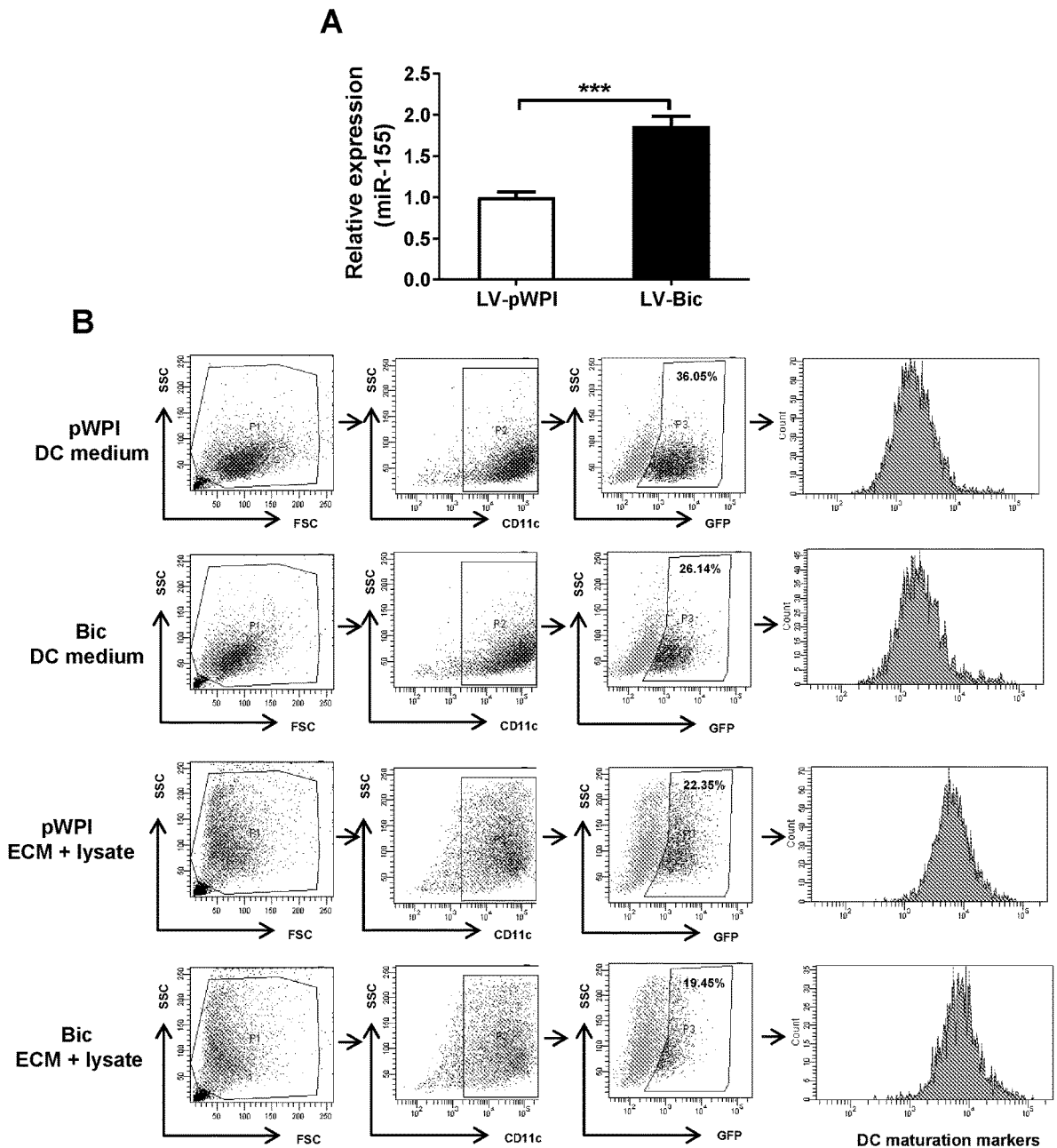
FIG. 16 shows characterization of miR-155 overexpressed BMDCs post lentivirus transduction.

FIG. 16 shows characterization of miR-155 overexpressed BMDCs post lentivirus transduction. Three days after lentivirus transduction, BMDCs were treated with tumor lysate and tumor conditioned medium for 48 h. (A) miR-155 expression level was quantified by RT-PCR. (B) GFP-positive DCs and their maturation status were determined by flow cytometry; representative scatter plots and histograms are shown.

Figure 17:
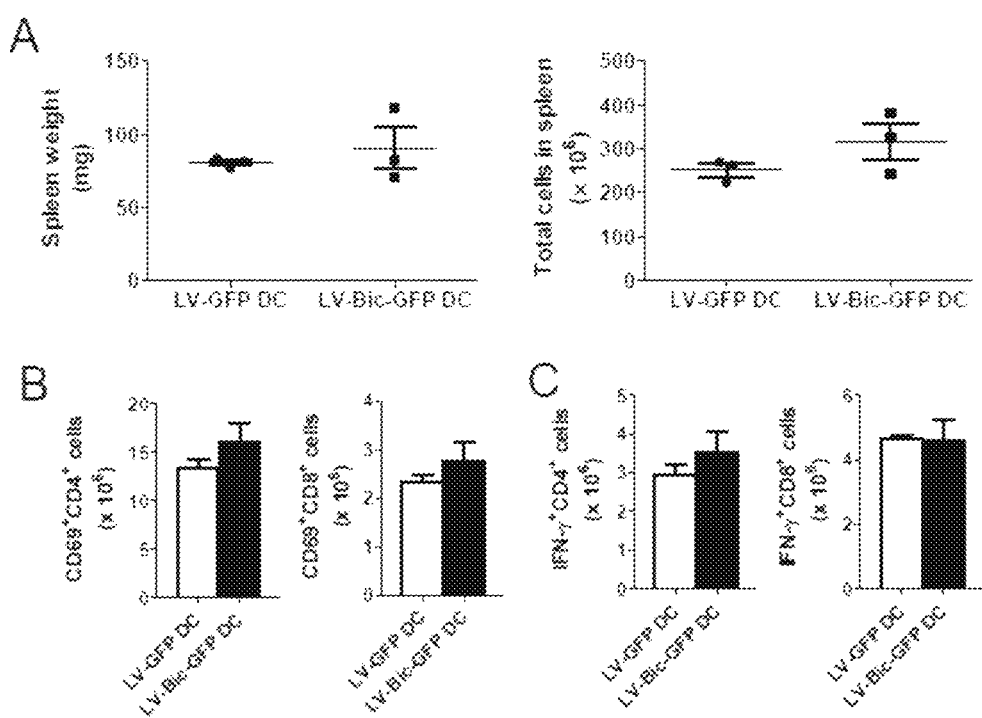
FIG. 17 shows T cell activation post miR-155 overexpressed BMDC immunization in vivo.

FIG. 17 shows T cell activation post miR-155 overexpressed BMDC immunization in vivo. Two days after transferring miR-155 overexpressed BMDCs into EO771 tumor bearing mice, spleens were removed and activated T cell (CD69+) content was determined by flow cytometry. (A) Spleen weight (left) and total leukocyte numbers (right) were quantified. Absolute numbers of activated T cells (B) and IN F-γ-producing T cells (C) were determined by flow cytometry. All data are presented as mean±SEM of 3 independent experiments.

The current disclosure, by applying an orthotopic breast cancer model, using an in vitro cell culture system mimicking the TME, and utilizing a lentiviral transduction system to force miR-155 overexpression in BMDCs, has demonstrated: 1) miR-155 is required for DCs to exert effective functions in the anti-tumor response, including maturation, cytokinesecretion, migration towards lymph nodes, and activation of T-cells; 2) tumor derived IL-6 and IL-10 can disrupt DC dynamics and function by compromising miR-155 induction in TME; and 3) forced overexpression of miR-155 in DCs may diminish the immunosuppressive effects of the TME and boost the functions of DCs in breast cancer.

It has been reported that during DC maturation by TLR ligands in various settings, suppression of miR-155 targets, such as SOCS-1, c-Fos, and Arg-2, is required for MHC II and costimulatory molecule expression as well as IL-12 production. The current disclosure demonstrates for the first time that m DCs display a profound defect in the ability to process and present tumor antigens to T cells in breast cancer accompanied by an accumulation of the aforementioned miR-155 targets. Upregulation of CCR7 expression is critical for driving mature DCs to migrate toward the T cell zone of draining lymph nodes. One of the major obstacles DC-based immunotherapy faces is that the migration of ex vivo pulsed DCs is defective. Correlation between CCR7 and miR-155 expression in DCs has been found in previous gene screening, but whether miR-155 regulates CCR7 expression on DCs in the context of cancer has not been reported. The current disclosure reveals that miR-155 can manipulate H3K27me3 enrichment at the CCR7 locus by targeting Jarid2, a direct miR-155 target, thus epigenetically upregulate CCR7 expression.

In many tumors, DCs remain immature, and thus are ineffective in inducing anti-tumor immunity. Tumor-derived soluble factors such as IL-6 and IL-10 are believed to impair DC functions in the TME. The current disclosure found that both IL-6 and IL-10 inhibited BMDCs maturation through depression of miR-155 upregulation, and their neutralizing antibodies de-repressed miR-155 upregulation and consequently promoted DC maturation, while the molecular mechanisms need further elucidation.

To investigate the translatability of the above findings, the current disclosure applied DC vaccines in a breast cancer model and revealed a diminished tumor-eliminating effect of a miR-155-/- DC vaccine. miR-155 upregulation in DCs is sufficient to break immune tolerance through targeting SHIP1 in the context of auto-immunity. The current disclosure's data, for the first time, shows that ex vivo achieved miR-155 overexpression substantially improved the anti-tumor efficacy of a DC-vaccine for breast cancer.

In summary, the current disclosure reveals a crucial role of DC miR-155 in initiating an effective anti-tumor immune response and suggested that boosting the expression of a single microRNA, miR-155, may significantly improve the efficacy of DC-based immunotherapies for breast cancer and possibly other solid tumors. Furthermore, an ex vivo DC engineering strategy to generate miR-155-based anti-cancer therapies can avoid the potential oncogenic side-effects of systemic miR-155 delivery. The ex vivo engineering methods may include, but not limited to, lentiviral or AAV transduction, electroporation or lipofectamine transfection, and liposomal or cationic polymer nanoparticle delivery.

Figure 18:
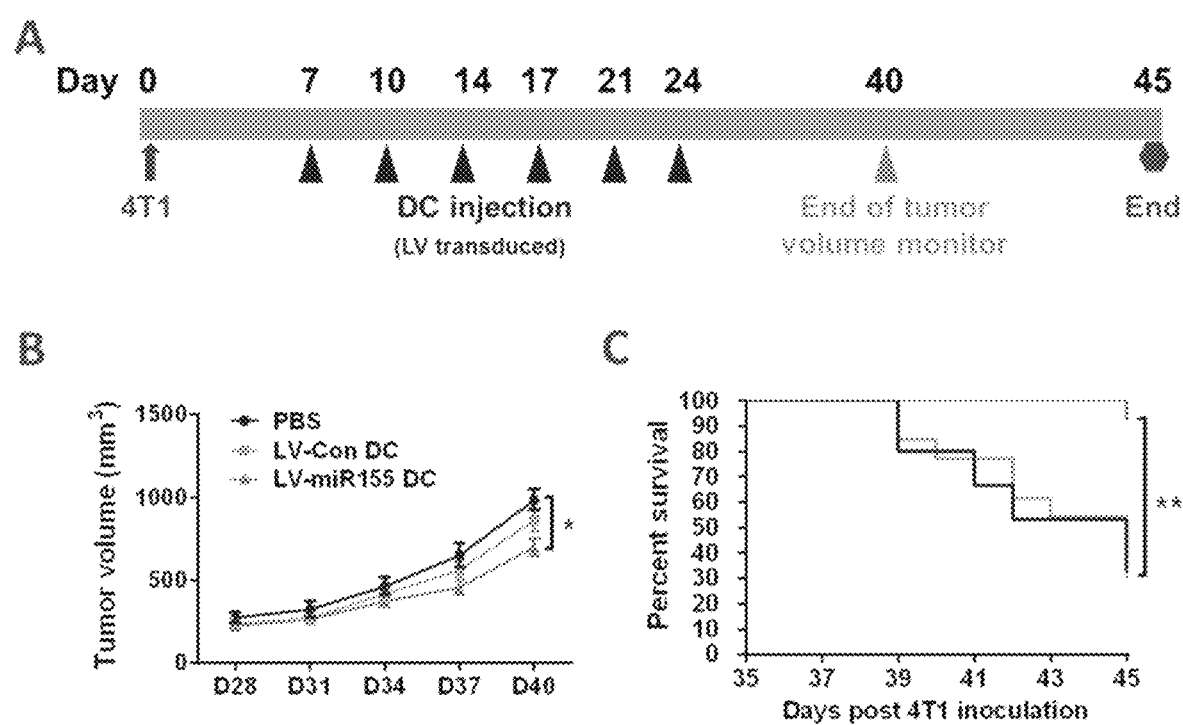
FIG. 18 shows that miR-155 overexpression boosts DC-based immunotherapy for breast cancer.

To examine if miR-155 overexpression in DCs enhances the anti-tumor efficacy of DC-based immunotherapy for breast cancer, WT Balb/c mice were implanted 4T1 cells at Day 0, and injected dendritic cell vaccines as depicted in FIG. 18, see Timeline A. The tumor growth was monitored as shown in FIG. 18, Graph B, and the survival of the mice was recorded as shown in Graph C of FIG. 18. The results showed that while DC vaccine using control lentivirus-transduced DCs did not halt the tumor growth and enhance mouse survival, DC vaccine using miR155-overexpressing DCs significantly suppressed the tumor growth and improved mouse survival.

As FIG. 18 shows, miR-155 overexpression boosts DC-based immunotherapy for breast cancer. The experimental design for the results shown in FIG. 18 includes: Timeline shows that 4T1 breast cancer cells (2×105) were injected into both sides of the 4th pair of mammary fat pads of 8-week-old female Balb/c mice (n=13-15 per group). At 7, 10, 14, 17, 21 and 21 days post cancer cell inoculation, 0.5×106 tumor-associated antigen pulsed BMDCs (from wild type Balb/c mice) transduced with miR155 lentiviruses or control lentiviruses in PBS, or equal volume of PBS were injected s.c. into mice as vaccines. See FIG. 18, Graph B. The tumor size was monitored till Day 40 post-inoculation. Data shows that miR155 lentivirus transduced DCs significantly inhibited tumor growth. See FIG. 18, Graph C. The survival of mice was monitored till Day 45 post-inoculation. Data shows that miR155 lentivirus transduced DCs significantly improved the survival of the tumor-bearing mice. *p<0.05.

Figure 19:
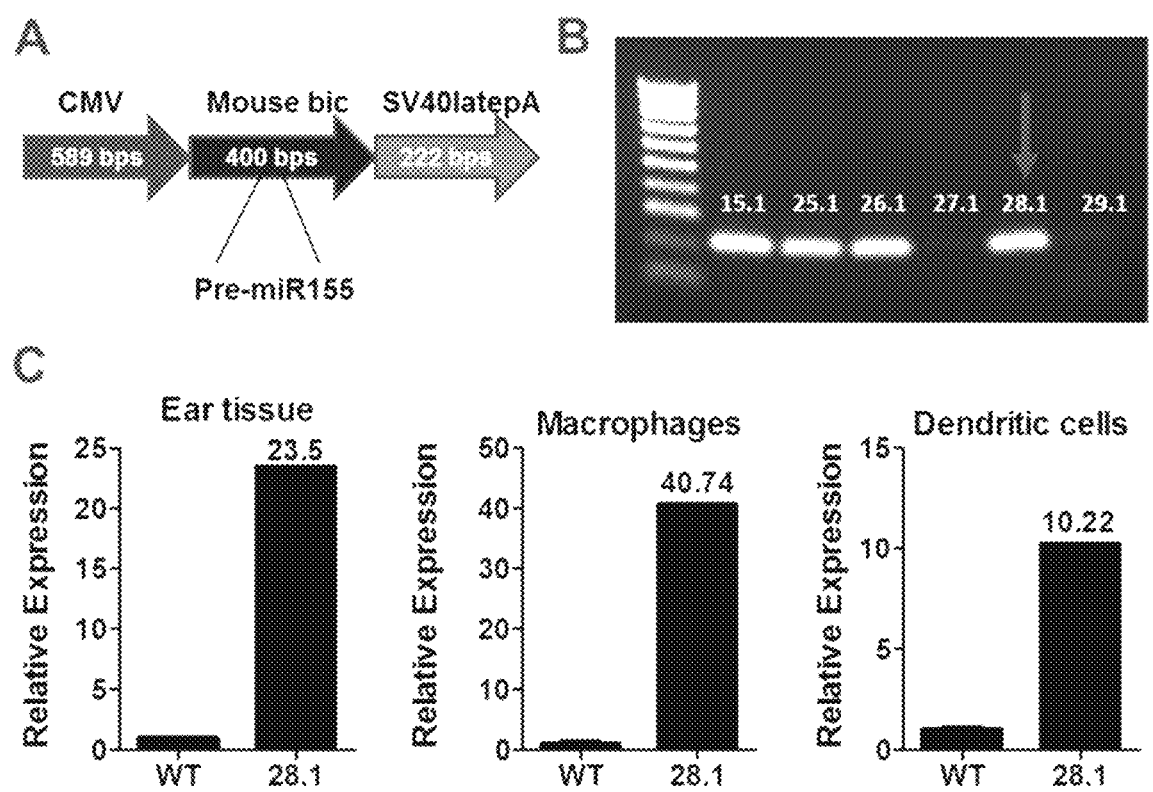
FIG. 19 shows generation and characterization of miR155 transgenic mice.

Transgenic mice overexpressing mouse miR155 were generated using a DNA construct as shown in FIG. 19, see Illustration A. Genotyping PCR confirmed the transgene insertion in the transgenic mice, see FIG. 19, image B, and qPCR confirmed the overexpression of mature miR155 in ear tissue, spleen derived macrophages and dendritic cells, see FIG. 19 Graphs at C. FIG. 19 at A shows a schematic drawing of the DNA fragment used for transgenic injection. FIG. 19 at B shows genotyping PCR to confirm the transgenic insertion. FIG. 19 at C shows qPCR confirmation of overexpression of miR155 in tissue and cells.

Figure 20:
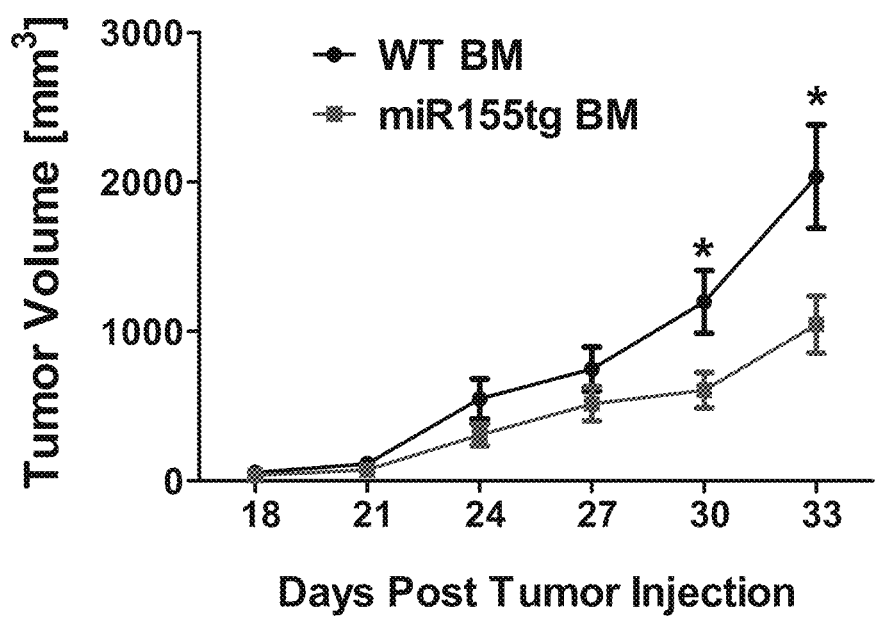
FIG. 20 shows that bone marrow cell miR155 overexpression suppresses breast tumor growth in mice.

Next, bone marrow cells from miR155 transgenic mice were transplanted into WT C57Bl/6 mice to generate chimeric mice with bone marrow-derived cells overexpressing miR155, then inoculated EO771 cells to these chimeric mice and the control mice receiving WT bone marrow cells. The results showed that the growth of breast tumors was significantly suppressed in the mice with miR155 overexpressing bone marrow cells, see FIG. 20. Although tumor growth suppressing effects of miR155-overexpressing bone marrow cells cannot be attributed only to DCs, this experiment, combined with the lentiviral transduction experiment, suggested that boosting miR155 expression in DCs and other bone marrow-derived cells may significantly enhance anti-tumor immunity in breast cancer, see FIG. 20. Bone marrow cell miR155 overexpression suppresses breast tumor growth in mice. Lethally irradiated female WT C57Bl/6 mice were transplanted with bone marrow cells from WT or miR155 transgenic mice. Four weeks later, the mice were inoculated with EO771 breast tumor cells and the tumor growth was monitored. *$p<0.05$, $n=5$. As FIG. 20 shows, bone marrow cell miR155 overexpression suppresses breast tumor growth in mice.

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art using the teachings disclosed herein.

What is claimed is:

1. A method for suppressing tumor growth:
amplifying a DNA fragment containing a microRNA;
sub-cloning the microRNA segment into a nanoparticle delivery vehicle;
delivering the micro-RNA segment to a cell via the delivery vehicle;
whereby delivery of the micro-RNA segment causes the cell to overexpress the micro-RNA;
injecting the cell into a tumor microenvironment; and
wherein overexpression of the micro-RNA segment by the cell suppresses breast cancer tumor growth;
wherein the microRNA segment comprises micro-RNA 155; and
wherein the cell receiving the micro-RNA segment is a bone marrow derived cell.

2. The method of claim 1, wherein the delivery vehicle for the micro-RNA segment comprises a viral vector.

3. The method of claim 2, wherein the viral vector comprises a lentivirus or an adenovirus.

4. The method of claim 1 wherein the micro-RNA segment is introduced to the cell via electroporation or lipofectamine transfection methods.

5. The method of claim 1, wherein the nanoparticle comprises a liposome or an ionic polymer nanoparticle.

6. A method for using a lentiviral vector to suppress tumor growth:
amplifying a DNA fragment containing a microRNA stem loop;
sub-cloning the DNA fragment containing the microRNA stem loop into a lentiviral vector;
delivering the lentiviral vector to a cell;
introducing the cell into a tumor microenvironment;
whereby delivery of the lentiviral vector containing the micro-RNA causes dendritic cell maturation followed by T-cell activation to suppress tumor growth;
wherein the tumor being suppressed is a breast cancer tumor;
wherein the microRNA stem loop comprises micro-RNA 155, and
wherein the cell is a bone marrow derived cell.

7. The method of claim 6, wherein the lentiviral vector comprises PWPI.

8. The method of claim 6, wherein the micro-RNA stem loop is introduced to the cell via electroporation or transfection.

9. The method of claim 1, wherein the method is used in association with at least one dendritic cell-based immunotherapy.

10. The method of claim 6, wherein the method is used in association with at least one dendritic cell-based immunotherapy.

* * * * *

SEQUENCE LISTING

<160> NUMBER OF SEQ ID NOS: 18

<210> SEQ ID NO 1
<211> LENGTH: 20
<212> TYPE: DNA
<213> ORGANISM: Mus musculus

<400> SEQUENCE: 1
gatgacatgg tgaagacggc                                               20

<210> SEQ ID NO 2
<211> LENGTH: 20
<212> TYPE: DNA
<213> ORGANISM: Mus musculus

<400> SEQUENCE: 2
aggcacaggg tcatcatcaa                                               20

<210> SEQ ID NO 3
<211> LENGTH: 20
<212> TYPE: DNA
<213> ORGANISM: Mus musculus

<400> SEQUENCE: 3
gagaaggtca cactggacca                                               20

<210> SEQ ID NO 4
<211> LENGTH: 20
<212> TYPE: DNA
<213> ORGANISM: Mus musculus

<400> SEQUENCE: 4
tgacctccac ctgtgagttc                                               20

<210> SEQ ID NO 5
<211> LENGTH: 20
<212> TYPE: DNA
<213> ORGANISM: Mus musculus

<400> SEQUENCE: 5
ttaacccggt actccgtgac                                               20

<210> SEQ ID NO 6
<211> LENGTH: 20
<212> TYPE: DNA
<213> ORGANISM: Mus musculus

```
<400> SEQUENCE: 6
gaggtctcca gccagaagtg                                            20

<210> SEQ ID NO 7
<211> LENGTH: 20
<212> TYPE: DNA
<213> ORGANISM: Mus musculus

<400> SEQUENCE: 7
gggctctcct gtcaacacac                                            20

<210> SEQ ID NO 8
<211> LENGTH: 20
<212> TYPE: DNA
<213> ORGANISM: Mus musculus

<400> SEQUENCE: 8
ctggtggaga tggctgtcac                                            20

<210> SEQ ID NO 9
<211> LENGTH: 20
<212> TYPE: DNA
<213> ORGANISM: Mus musculus

<400> SEQUENCE: 9
ctgtgtcacc atgggaggag                                            20

<210> SEQ ID NO 10
<211> LENGTH: 20
<212> TYPE: DNA
<213> ORGANISM: Mus musculus

<400> SEQUENCE: 10
gcatgagcat caacccagat                                            20

<210> SEQ ID NO 11
<211> LENGTH: 20
<212> TYPE: DNA
<213> ORGANISM: Mus musculus

<400> SEQUENCE: 11
cgcggttcta ttttgttggt                                            20

<210> SEQ ID NO 12
<211> LENGTH: 20
<212> TYPE: DNA
<213> ORGANISM: Mus musculus

<400> SEQUENCE: 12
agtcggcatc gtttatggtc                                            20

<210> SEQ ID NO 13
<211> LENGTH: 23
<212> TYPE: RNA
<213> ORGANISM: Mus musculus

<400> SEQUENCE: 13
uuaaugcuaa uugugauagg ggu                                        23

<210> SEQ ID NO 14
<211> LENGTH: 22
<212> TYPE: RNA
```

```
<213> ORGANISM: Mus musculus

<400> SEQUENCE: 14
cgcaaggaug acacgcaaau uc                                              22

<210> SEQ ID NO 15
<211> LENGTH: 20
<212> TYPE: DNA
<213> ORGANISM: Mus musculus

<400> SEQUENCE: 15
tcccacccct cagagtcttc                                                 20

<210> SEQ ID NO 16
<211> LENGTH: 20
<212> TYPE: DNA
<213> ORGANISM: Mus musculus

<400> SEQUENCE: 16
gggctttctg aaggcaaacg                                                 20

<210> SEQ ID NO 17
<211> LENGTH: 20
<212> TYPE: DNA
<213> ORGANISM: Mus musculus

<400> SEQUENCE: 17
tggtgagcgg aactctagga                                                 20

<210> SEQ ID NO 18
<211> LENGTH: 20
<212> TYPE: DNA
<213> ORGANISM: Mus musculus

<400> SEQUENCE: 18
gctccagaca ccccagttac                                                 20
```